US009026190B2

(12) United States Patent
Shenasa et al.

(10) Patent No.: US 9,026,190 B2
(45) Date of Patent: May 5, 2015

(54) PORTABLE PHYSIOLOGICAL PARAMETER DETECTION AND MONITORING DEVICE WITH INTEGRATABLE COMPUTER MEMORY AND COMMUNICATION DISK, SYSTEMS AND METHODS OF USE THEREOF

(75) Inventors: Mohammad Shenasa, Monte Sereno, CA (US); Shahid K. Siddiqui, Saratoga, CA (US); Naeem M. Ansari, Santa Clara, CA (US)

(73) Assignee: Rhythm Check, Inc., Santa Clara, CA (US)

( * ) Notice: Subject to any disclaimer, the term of this patent is extended or adjusted under 35 U.S.C. 154(b) by 475 days.

(21) Appl. No.: 13/297,886

(22) Filed: Nov. 16, 2011

(65) Prior Publication Data

US 2012/0265026 A1    Oct. 18, 2012

Related U.S. Application Data

(60) Provisional application No. 61/414,771, filed on Nov. 17, 2010, provisional application No. 61/435,319, filed on Jan. 23, 2011.

(51) Int. Cl.
*A61B 5/0404* (2006.01)
*A61B 5/00* (2006.01)
*A61B 5/0408* (2006.01)
*G06F 19/00* (2011.01)

(52) U.S. Cl.
CPC .............. *A61B 5/0022* (2013.01); *A61B 5/0404* (2013.01); *A61B 5/0006* (2013.01); *A61B 5/0408* (2013.01); *A61B 5/6898* (2013.01); *G06F 19/3406* (2013.01); *G06F 2213/0038* (2013.01)

(58) Field of Classification Search
CPC .. A61B 5/6898; A61B 5/0002; A61B 5/0022; A61B 5/02; A61B 5/024; A61B 5/02438; A61B 5/02444; A61B 5/04; A61B 5/0402; A61B 5/0404; A61B 5/0408; A61B 5/04085; A61B 5/053; A61B 5/0531; A61B 5/6825; A61B 5/6826; A61B 5/6843; A61B 5/6897; A61B 2560/0468; A61B 2562/0209; A61B 2562/0214; A61B 2562/24–2562/247
USPC ................. 600/372, 382, 391, 393, 301, 509; 340/573.1
See application file for complete search history.

(56) References Cited

U.S. PATENT DOCUMENTS

| 3,565,694 | A | | 2/1971 | Chireau |
| 4,359,726 | A | * | 11/1982 | Lewiner et al. ............... 340/666 |
| 4,564,433 | A | | 1/1986 | Werdecker et al. |
| 6,219,569 | B1 | | 4/2001 | Kelly et al. |
| 6,416,471 | B1 | | 7/2002 | Kumar et al. |

(Continued)

FOREIGN PATENT DOCUMENTS

WO    2012068337 A3    5/2012

*Primary Examiner* — Lee S Cohen
*Assistant Examiner* — Erin M Cardinal
(74) *Attorney, Agent, or Firm* — Shartsis Friese LLP; Cecily Anne O'Regan

(57) ABSTRACT

Methods, devices and kits for monitoring a physiological parameter using a portable physiological parameter detection and monitoring device. The devices include a removably adherable transparent film with an insulating upper surface that has two or more conductive elements within the film. The film can be adhered to a mobile device, such as a cell phone, to facilitate detecting a biological parameter such as a heart rhythm.

21 Claims, 17 Drawing Sheets

(56) References Cited

U.S. PATENT DOCUMENTS

| | | |
|---|---|---|
| 7,630,756 B2 | 12/2009 | Linker |
| 7,680,532 B2 | 3/2010 | Wiesel |
| 7,715,907 B2 | 5/2010 | Koertge et al. |
| 7,740,627 B2 | 6/2010 | Gammie et al. |
| 7,749,157 B2 | 7/2010 | Bertolero |
| 7,783,352 B1 | 8/2010 | Ryu et al. |
| 7,799,025 B2 | 9/2010 | Wellman |
| 8,700,137 B2 * | 4/2014 | Albert ............... 600/513 |
| 2003/0110613 A1 | 6/2003 | Ross |
| 2003/0129355 A1 | 7/2003 | Ross |
| 2004/0015096 A1 | 1/2004 | Mok et al. |
| 2004/0059205 A1 | 3/2004 | Carlson et al. |
| 2006/0020216 A1 * | 1/2006 | Oishi et al. ............... 600/500 |
| 2006/0264730 A1 * | 11/2006 | Stivoric et al. ........... 600/390 |
| 2006/0292039 A1 * | 12/2006 | Iida ........................ 422/82.05 |
| 2007/0167859 A1 * | 7/2007 | Finneran et al. ......... 600/546 |
| 2008/0177154 A1 | 7/2008 | Hansen et al. |
| 2010/0152794 A1 * | 6/2010 | Radivojevic et al. ......... 607/2 |
| 2010/0254581 A1 * | 10/2010 | Neeser et al. .............. 382/128 |
| 2011/0015496 A1 * | 1/2011 | Sherman et al. ........... 600/301 |
| 2011/0301435 A1 * | 12/2011 | Albert et al. .............. 600/301 |
| 2012/0022385 A1 * | 1/2012 | Shimuta et al. ........... 600/509 |
| 2012/0116176 A1 * | 5/2012 | Moravec et al. .......... 600/300 |
| 2012/0310071 A1 * | 12/2012 | Nakao et al. .............. 600/393 |

\* cited by examiner

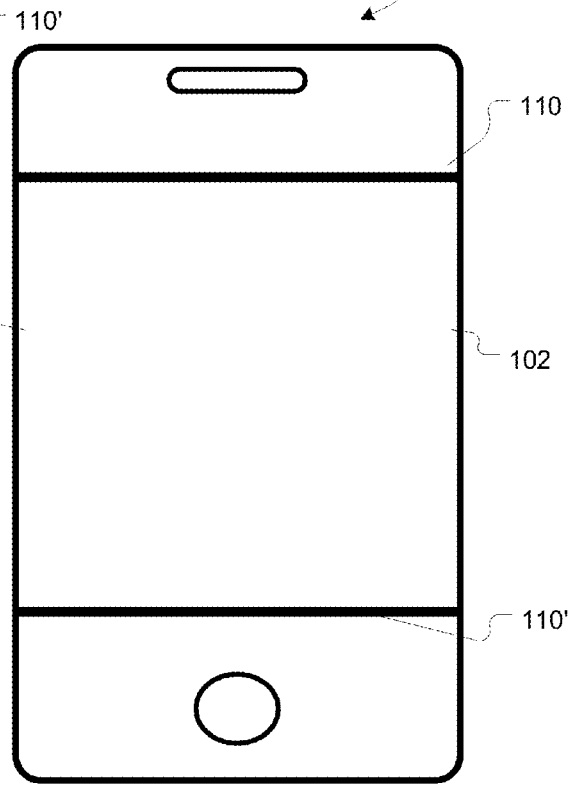
Figure 1A
Figure 1B

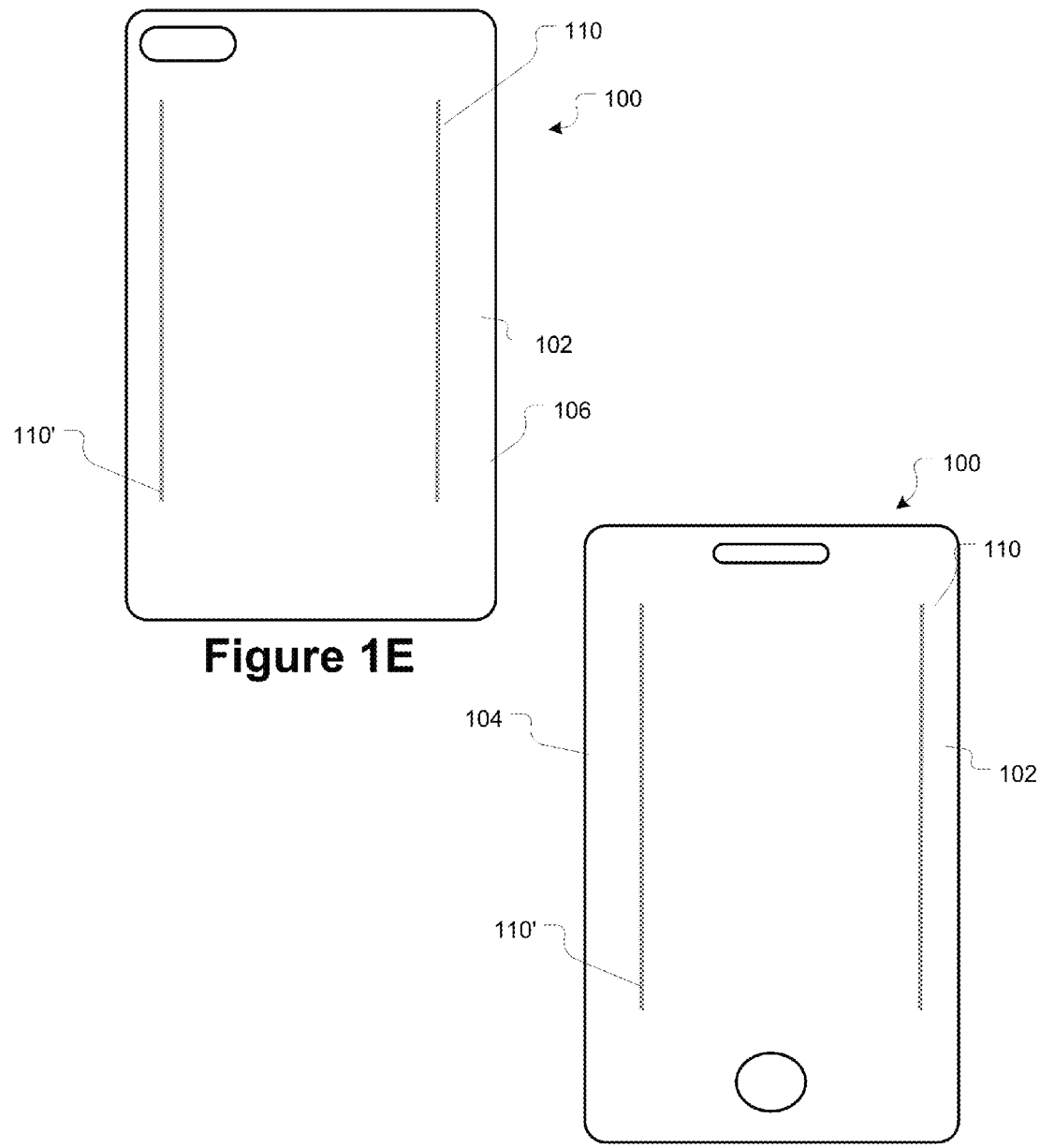

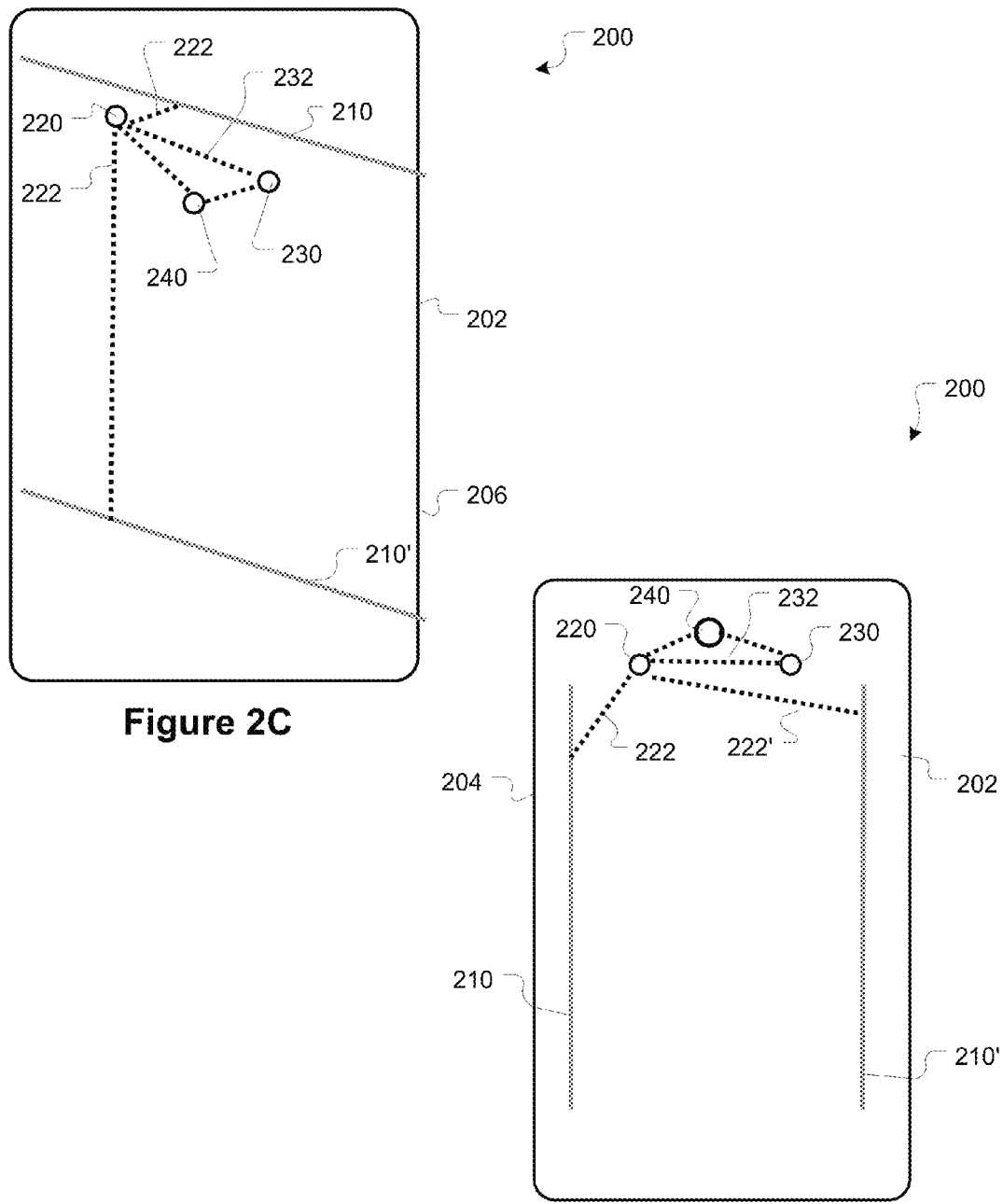

PORTABLE PHYSIOLOGICAL PARAMETER DETECTION AND MONITORING DEVICE WITH INTEGRATABLE COMPUTER MEMORY AND COMMUNICATION DISK, SYSTEMS AND METHODS OF USE THEREOF

CROSS-REFERENCE

This application claims the benefit of U.S. Provisional Application No. 61/414,771, entitled Portable Heart Rhythm Detection Devices, Systems and Methods, filed Nov. 17, 2010, and 61/435,319, entitled Portable Physiological Parameter Detection and Monitoring Device with Integrated Computer Memory and Communication Disk Systems and Methods of Use Thereof filed Jan. 23, 2011, which applications are incorporated herein by reference.

BACKGROUND OF THE INVENTION

1. Field

The present disclosure generally relates to portable medical devices which consist of physiological parameter detection devices having two or more electrodes incorporated therein.

2. Background

Atrial fibrillation (AF) is a cardiac arrhythmia, i.e. an altered electrical activity (irregular or faster or slower than normal) of the heart, that involves the atria, and is an example of one type of cardiac rhythm that would benefit from remote monitoring. AF may be detected as irregularities when taking a pulse. Rhythm disturbances i.e. arrhythmias are common, and often asymptomatic so called "silent" which at times may be life threatening. Accurate detection and diagnosis is warranted as well as monitoring. AF is the most common form of arrhythmia affecting approximately 3-5% of people over 65 and 8% of people over 80. For example, there are about 2.2 million cases in the U.S. yearly. It is a highly prevalent disease associated with significant cardiovascular morbidity and mortality. AF represents 34% of hospitalizations in the U.S. for arrhythmias annually. It is estimated that the annual cost to the U.S. Medicare system alone is more than $15.7 billion due to cost complications. However, screening and diagnosis is limited in the Medicare population. By 2015, it is projected that 15 million Americans will suffer from AF and its adverse consequences.

In AF, the electrical impulses that are normally generated by the sinoatrial node (the sinus node) are replaced by disorganized activity in the atria, leading to irregular conduction of impulses to the ventricles that generate the heartbeat. This results in irregular heartbeats. AF may be continuous (persistent or permanent AF) or alternating between periods of normal heart rhythm (paroxysmal AF). Over time, the natural tendency of AF is to become continuous/chronic. The type of AF considered to be most dangerous is paroxysmal AF because the recurrent onsets and offsets of fibrillation increase the probability of embolization significantly. During an AF episode, the blood is rather stationary in the atria and coagulation forming blood clots may take place. When the activity then returns to normal, the clots are propelled out into the cardiovascular system, potentially causing strokes etc. Further, paroxysmal AF is the type of AF that normally occurs first, i.e. it is rather unusual that a healthy subject immediately enters chronic AF. AF is a rhythm disturbance having many etiologies (causes) which include, for example, high blood pressure, diabetes, heart failure, etc. In particular AF is a common complication of heart failure. On the other hand AF in the long run may also cause or precipitate heart failure, therefore a timely detection and management is critical.

It should also be noted that out-patients with AF typically also have heart disease (about 65%). More alarmingly, though, is that AF is also associated with silent stroke, dementia and Alzheimer's disease. Stroke affects about 795,000 people annually in the U.S. (about 1 stroke every 40 seconds) and is the third leading cause of death and the number one cause of disability.

There remains a need for an improved device and method for early and convenient detection of AF and for portable and convenient devices capable of monitoring a cardiac rhythm.

Other concepts relating to the disclosure are disclosed in, for example, U.S. Pat. No. 3,565,694 to Chireau for Bipolar Electrode and Method of Making Same; U.S. Pat. No. 4,564,433 to Werdecker et al. for Bipolar Electrode; U.S. Pat. No. 6,416,471 B1 to Kumar et al. for Portable Remote Patient Telemonitoring System; U.S. Patent Publication US 2003/0110613 A1 to Ross for Screen Protector; and U.S. Patent Publication US 2003/0129355 A1 to Ross for Screen Protector.

SUMMARY OF THE INVENTION

The current disclosure provides for a low profile portable detection device adapted and configured to obtain a physiological parameter from a mammal and either store the captured signals on a mobile device, such as a cell phone, smart phone (similar to but not limited to iPhone®), or transmit the data via a communication network such as LAN, WAN and Wifi, mWifi, radio frequency (RF) or any other wireless medium to another location.

The detection device can also be configured to include a storage disk, a logic device, software, a power source, and one or more chips such as a wireless communication chip which can be adapted and configured to be in communication with, for example, a smart phone (iPhone®, Blackberry® or similar smart phone device) and/or a communication network and a GPS chip. Communication can be made with any device capable of detecting and capturing one or more physiological parameters. Physiological parameters include, but are not limited to, impedance, cardiac rhythm disturbances e.g., arrhythmias that are common, and often asymptomatic so called "silent" which at times may be life threatening, pulse and/or any other desired physiological parameter. Other physiological characteristics include temperature, respiration, blood pressure, vasomotor activity, physical activity, and body position. The physiological parameter detection device can be adapted and configured to also monitor one or more physiological parameters (e.g., impedance, heart rhythm and/or pulse) over a period of time, both on a long-term basis and an intermittent basis. The detection devices can operate on a standalone basis or as part of a communication network. The detection devices can be configured to be re-usable.

An aspect of the disclosure is directed to a detection device adapted to capture a physiological parameter. Detection devices comprise: a transparent film with an insulating upper surface and a lower surface characterized in that it is removeably adherable; two or more conductive elements wherein at least two conductive elements of the two or more conductive elements are bipolar electrodes, in electrical communication with the removeably adherable lower surface and electrically isolated by the insulating upper surface. Detection devices typically include two or more conductive elements. The two or more conductive elements can further be configured to include a first elongated conductive element and a second elongated conductive element, electrically separated from the first elongated conductive element. Moreover, the transparent film can be configured such that it has a dimension of from about 40 cm² to 150 cm² in two dimensions and is at least one of square and rectangular. Although other sizes and configurations are possible without departing from the scope of the disclosure. In some configurations, the first elongated conductive element and a second elongated conductive element are configurable within the film such that they are one or more of positioned at opposing ends of the film, parallel each other in a plane, and/or have a shape selected from the group comprising elongated, bracket, and curved. In other configurations, the detection device can further be configured to have one or more of computer memory, microchip, connector, power source, GPS chip, WiFi chip, communication chip.

Another aspect of the disclosure is directed to a method for monitoring a physiological parameter. The method comprises: providing a detection device having a transparent film with an insulating upper surface and a lower surface characterized in that it is removeably adherable, two or more conductive elements wherein at least two conductive elements of the two or more conductive elements are bipolar electrodes, in electrical communication with the removeably adherable lower surface and electrically isolated by the insulating upper surface; placing the film in contact with a mammalian surface having one or more detectable physiological characteristics; acquiring one or more detectable physiological characteristics; and at least one of storing the one or more detectable physiological characteristics on a memory and transmitting the one or more detectable physiological characteristics to another location. The method can also include the step of activating the step of acquiring the one or more detectable physiological characteristics. In some configurations, the step of transmitting the one or more detectable physiological characteristics can further include transmitting the one or more detectable physiological characteristics to one or more of a hospital, a rhythm monitoring center, and a doctor's office, an electronic device, and a computer. Additionally, the method can include the step of activating a software application associated with an electronic device. In at least some aspects the detectable physiological characteristics are one or more of impedance, heart rhythm and/or pulse. Other physiological characteristics include temperature, respiration, blood pressure, vasomotor activity, physical activity, and body position. In some aspects the step of acquiring is performed at least one of continuously and intermittently while the detection device is in electrical communication with the mammalian surface. Additionally, the method can include the step of removing the detection device from an electronic device.

A further aspect of the disclosure is directed to a kit for physiological characteristic detection. The kit is configurable to comprise one or more of the following: a detection device having a transparent film with an insulating upper surface and a lower surface characterized in that it is removeably adherable, two or more conductive elements wherein at least two conductive elements of the two or more conductive elements are bipolar electrodes, in electrical communication with the removeably adherable lower surface and electrically isolated by the insulating upper surface; a software application; alcohol swabs; and a lint cloth.

Yet another aspect of the disclosure is directed to a networked apparatus. The networked apparatus comprises: a memory; a processor; a communicator; a display; and a detection device having a transparent film with an insulating upper surface and a lower surface characterized in that it is removeably adherable, two or more conductive elements wherein at least two conductive elements of the two or more conductive elements are bipolar electrodes, in electrical communication with the removeably adherable lower surface and electrically isolated by the insulating upper surface.

Still another aspect of the disclosure is directed to a communication system. The communication system of the disclosure comprises: a detection device having a transparent film with an insulating upper surface and a lower surface characterized in that it is removeably adherable, two or more conductive elements wherein at least two conductive elements of the two or more conductive elements are bipolar electrodes, in electrical communication with the removeably adherable lower surface and electrically isolated by the insulating upper surface; a server computer system; a measurement module on the server computer system for permitting the transmission of a measurement from a detection device over a network; at least one of an API (application program interface) engine connected to at least one of the detection device to create a message about the measurement and transmit the message over an API integrated network to a recipient having a predetermined recipient user name, an SMS (short message service) engine connected to at least one of the system for detecting physiological parameters and the detection device to create an SMS message about the measurement and transmit the SMS message over a network to a recipient device having a predetermined measurement recipient telephone number, and an email engine connected to at least one of the detection device to create an email message about the measurement and transmit the email message over the network to a recipient email having a predetermined recipient email address. A storing module on the server computer system for storing the measurement in a detection device server database can also be provided. In some system configurations, the detection device is connectable to the server computer system over at least one of a mobile phone network and an Internet network, and a browser on the measurement recipient electronic device is used to retrieve an interface on the server computer system. In still other configurations, the system further comprising: an interface on the server computer system, the interface being retrievable by an application on the mobile device. Additionally, the server computer system can be configured such that it is connectable over a cellular phone network to receive a response from the measurement recipient mobile device. The system can further comprise: a downloadable application residing on the measurement recipient mobile device, the downloadable application transmitting the response and a measurement recipient phone number ID over the cellular phone network to the server computer system, the server computer system utilizing the measurement recipient phone number ID to associate the response with the SMS measurement. Additionally, the system can be configured to comprise: a transmissions module that transmits the measurement over a network other than the cellular phone SMS network to a measurement recipient user computer system, in parallel with the measurement that is sent over the cellular phone SMS network.

Yet another aspect of the disclosure is directed to a networked apparatus. The networked apparatus is configurable to comprise: a memory; a processor; a communicator; a display; and a detection device having a transparent film with an insulating upper surface and a lower surface characterized in that it is removeably adherable, two or more conductive elements wherein at least two conductive elements of the two or more conductive elements are bipolar electrodes, in electrical communication with the removeably adherable lower surface and electrically isolated by the insulating upper surface.

In another aspect of the disclosure, a communication system is provided. The communication system is configurable to comprise: a detection device having a transparent film with an insulating upper surface and a lower surface characterized in that it is removeably adherable, two or more conductive elements wherein at least two conductive elements of the two or more conductive elements are bipolar electrodes, in electrical communication with the removeably adherable lower surface and electrically isolated by the insulating upper surface; a server computer system; a measurement module on the server computer system for permitting the transmission of a measurement from a system for detecting physiological characteristics over a network; at least one of an API engine connected to the detection device to create an message about the measurement and transmit the message over an API integrated network to a recipient having a predetermined recipient user name, an SMS engine connected the detection device to create an SMS message about the measurement and transmit the SMS message over a network to a recipient device having a predetermined measurement recipient telephone number, and an email engine connected to the detection device to create an email message about the measurement and transmit the email message over the network to a recipient email having a predetermined recipient email address. Additionally, in at least some configurations, the system comprises a storing module on the server computer system for storing the measurement on detection device server database. In other aspects, the detection device can be configured such that it is connectable to the server computer system over at least one of a mobile phone network and an Internet network, and a browser on the measurement recipient electronic device is used to retrieve an interface on the server computer system. The measurement recipient can be an electronic device is connected to the server computer system over a cellular phone network. In some configurations of the system, the measurement recipient electronic device is a mobile device.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-J illustrate a variety of configurations suitable for a detection device for use in conjunction with an electronic device;

FIGS. 2A-F illustrate a variety of configurations suitable for the detection device which is usable on a stand-alone basis;

DETAILED DESCRIPTION OF THE INVENTION

Figures 1C, 1D:
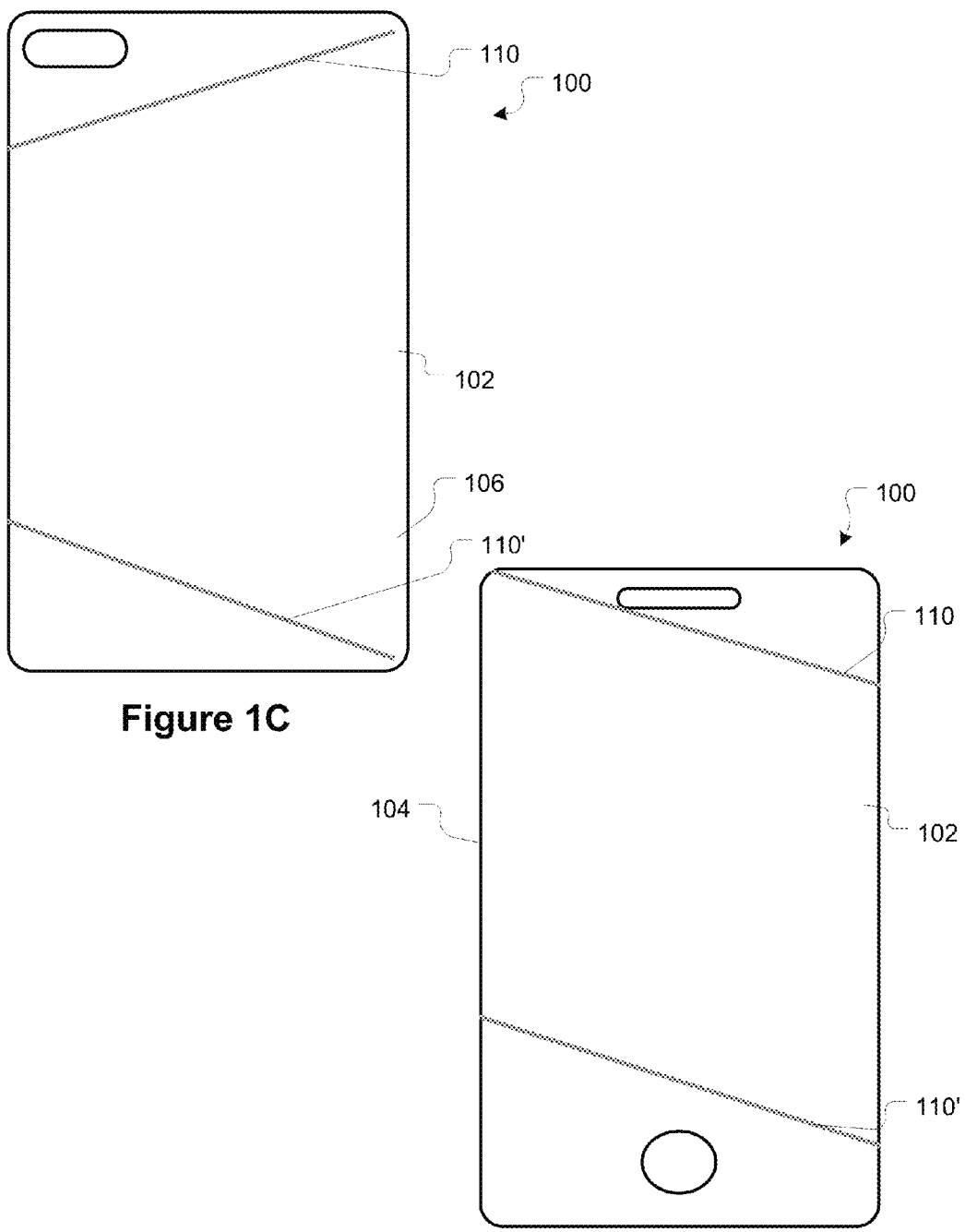

In order to appreciate the novelty of the disclosure, it is important to understand the basics of the human conduction system of the heart. The normal human conduction system carries an impulse from the atria to the ventricles and distributes the electrical impulse very efficiently so that the entire ventricle is electrically activated in less than 100 milliseconds. This permits effective ventricular contraction. Normal ventricular conduction mechanism starts with a bridge from the atrium to the ventricles called the atrio-ventricular node (AV node). The AV node is activated by the sino-atrial node (SA node). Once an impulse passes through the AV node, the impulse then passes through the bundle of His, which is at the base of the ventricles. Thereafter, the conduction system divides into a left main branch and right main branch. The left branch, which activates the left ventricle, almost immediately divides into a small anterior branch and a much larger posterior branch of the left main branch that swings around the left ventricle and basically surrounds the posterior mitral annulus before it spreads out over the ventricles. The posterior branch activates the left ventricle summit early in systole and starts the process by which the mitral valve closes. Rhythm disturbances in this system are common, and often asymptomatic (or silent) arrhythmias may be life threatening. Accurate detection and diagnosis is warranted. Symptomatic cases are often paroxysmal and detection is often hit or miss with currently available technology. Devices and methods for treatment and detection of AF, for example, are disclosed in, for example, U.S. Pat. No. 7,799,025 for Surgical Treatment for Atrial Fibrillation Using Radiofrequency Technology; U.S. Pat. No. 7,783,352 for Optimizing anti-tachychardia Pacing for Terminating Atrial Fibrillation; U.S. Pat. No. 7,749,157 for Methods and Devices for Minimally Invasive Cardiac Surgery for Atrial Fibrillation; U.S. Pat. No. 7,740,627 for Surgical Method and Apparatus for Treating Atrial Fibrillation; U.S. Pat. No. 7,715,907 for Method and System for Atrial Fibrillation Analysis, Characterization and Mapping; U.S. Pat. No. 7,680,532 for Detective Atrial Fibrillation, Method of and Apparatus For; and U.S. Pat. No. 7,630,756 for Long-Term Monitoring for Detection of Atrial Fibrillation.

The goals of AF management are to: (1) restore normal rhythm (sinus rhythm); (2) prevent recurrences of AF; (3) abolish the risk of stroke; (4) improve the quality of life for the patient; and (5) improve survival.

Most patients with AF require long term anticoagulation to prevent stroke and antiarrhythmic medication to restore sinus rhythm and/or prevent recurrences. Over the past decade transcatheter ablation of AF, particularly in the paraxsysmal form has been used to cure the arrhythmias in about 70% of the cases. Although, the problem of silent AF has long been recognized, AF detection, especially post ablation, is of great interest. Current technologies lack the ability to obtain immediate snapshots of the cardiac rhythm that could readily be available to the patient and health care provider.

Holter monitor, event recorders and implantable loop recorders do not provide immediate results. Furthermore, all of them constitute more than one step of detection recording and transmission. A device, as described herein, can be configured to provide noninvasive, real-time EKG recording with immediate wireless transmission. Our system is a simple device recording and is as simple as taking a picture on any smart phone system and emailing it or transmitting it to designated receivers and can also be saved on smart phone's memory like photos. Furthermore, AF is an age dependent rhythm disturbances, so as stroke. Although, there has been a decline in age adjusted rate of stroke with aging population, this implies that the absolute number of strokes and AF may increase over the next two decades, as the relationship between "Silent" AF and "Silent" embolic (cryptogenic) Stroke is becomes more apparent.

The description provided herein has been made using arrhythmia and heart rhythm detection as an example of a physiological parameter suitable for measurement. However, as will be appreciated by those skilled in the art, the present disclosure is not limited to this type of physiological monitoring but can also be applied to other physiological and health monitoring parameters, including, for example, temperature, respiration, blood pressure, vasomotor activity, physical activity, and body position.

I. Detection Devices and Systems

FIGS. 1A-J illustrate a variety of configurations suitable for a detection device. The detection device 100 is formed from a protective transparent film 102 having a first side 104 and a second side 106 two or more electrodes 110, 110'. The electrodes can be added to the film during the manufacturing process. Electrodes can be made of any suitable conductive material including, but not limited to aluminum, copper, silver and gold. The protective film can be made of any suitable material capable of sticking or adhering, removeably sticking or adhering, or repeatably sticking or adhering to a surface of a target electronic device, such as a cell phone 808 or smart phone or other portable smart device. The protective transparent film can be made from, for example, polyester films, polyolef in films, polyvinyl chloride films, acrylic films, methacrylic films, styrenic films, ceramic films, glass films and suitable co-polymers thereof.

The two or more electrodes can be elongated electrodes, as illustrated, wherein at least two of the electrodes are bipolar electrodes. In most configurations, the electrodes are sized to enable the electrodes to detect a physiological parameter. Where the detection device is positionable on a screen of an electronic device, the electrodes may also be elongated to minimize visual impairment of the electronic device screen.

One surface of the film typically includes a resin disposed on the surface. Moreover, the film can be a biaxially oriented polyethylene terephthalate film that includes a cured, roughened coating on the second surface 106 that contacts, for example, the electronic screen 898 or housing of the smart phones (similar to but not limited to iPhone®), or smart device 808 and a scratch resistant coating disposed on the outer surface 104. The scratch resistant coating can also function as a writing surface where the device is positioned on the screen. The outer (upper) surface of the film also functions as an insulating cover.

During the process of manufacturing a suitable film, two or more electrodes can be added to the film (either on a surface or embedded) in such a way that at least a portion of the electrodes are exposed on the surface of the film or the film can also have a coating of adhesive layer containing the active material of opposite distributed there through in finely comminuted form. The polymeric matrix of this coating, apart from adhering firmly to the metal and must be sufficiently conductive to form of low resistance internal current path between the two electrodes plate surface. The two or more electrodes are then accessible by a user from the under (lower) surface of the film by touching them, e.g. with a hand, or placing the lower surface against a mammalian body. In other configurations, the electrodes can be attached to the film in a post-processing or during the film making process step.

The shape of the film can vary such that it is square, rectangular, round, oval, elliptical, diamond, etc. In at least some embodiments, the shape will take on the shape of the mobile device to which the film is attached. The dimension of the film typically range from about 40 $cm^2$ to 150 $cm^2$ in two dimensions. However, other dimensions can be used to accommodate different sized electronic devices (e.g., tablet computers) or to take into consideration different physiological accommodations.

Figures 1G, 1H:
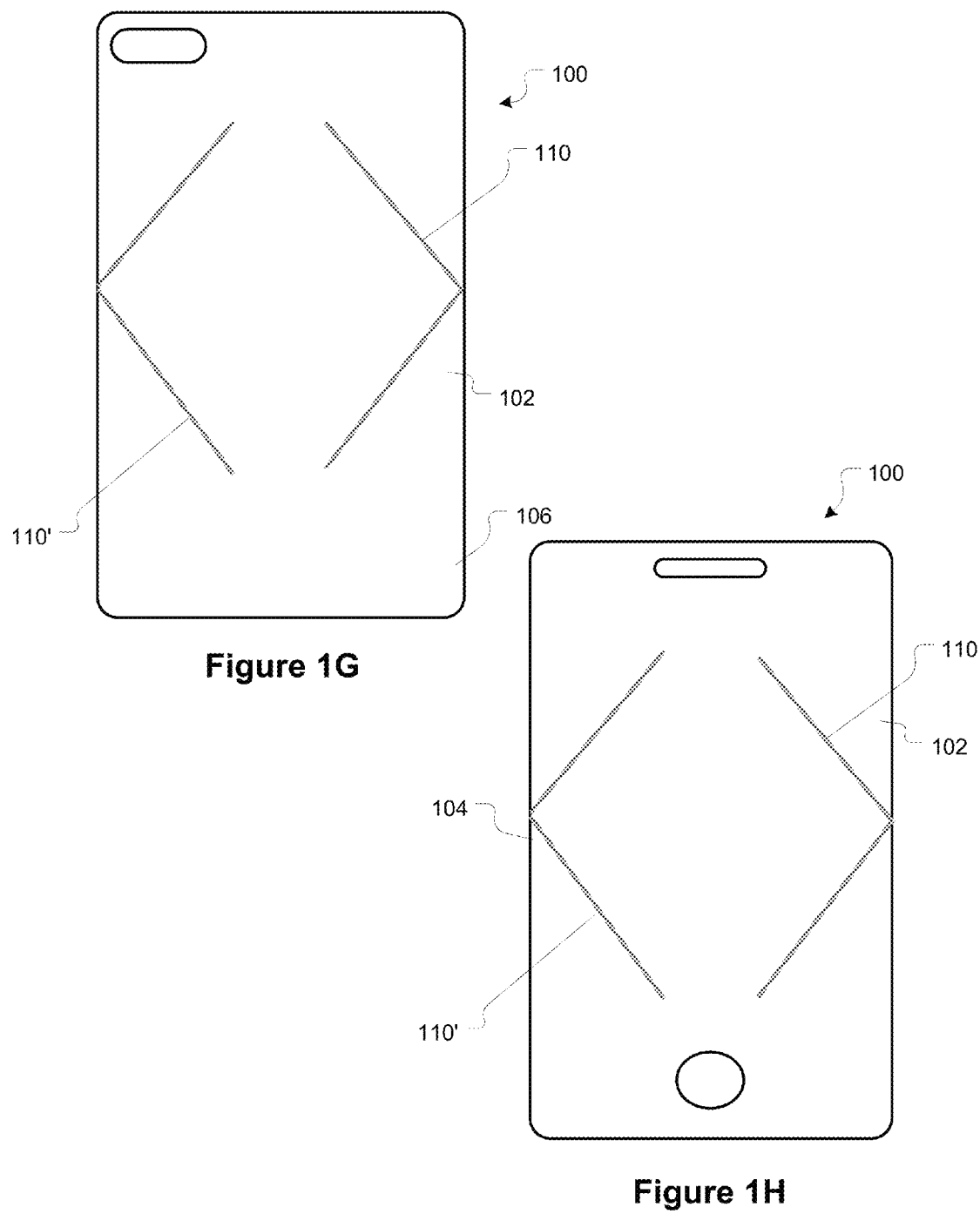
Figures 1I, 1J:
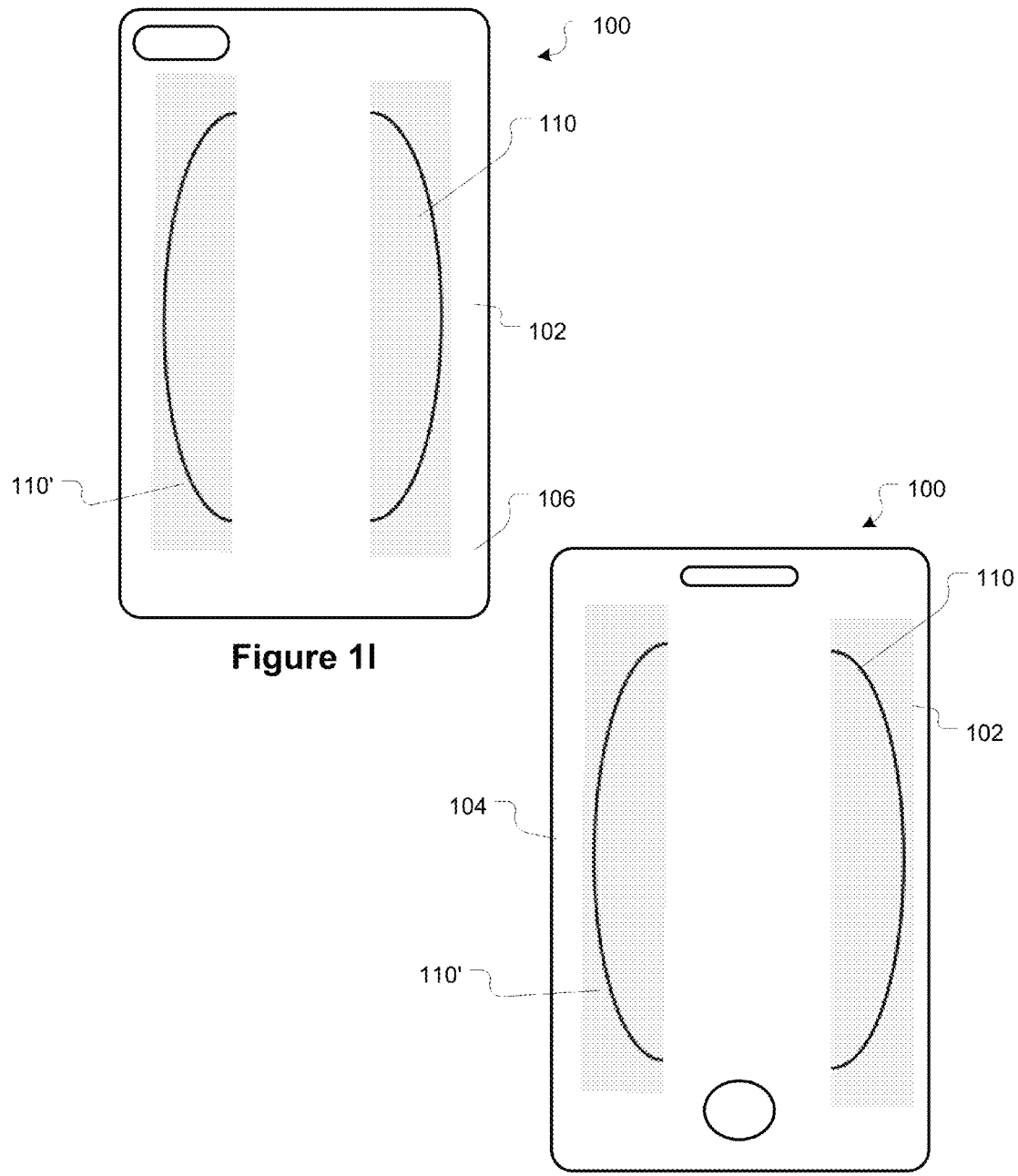

As further illustrated in FIGS. 1A-J the positioning of the two or more electrodes within the film can also take on a wide variety of configurations including, but not limited to, parallel across a top and bottom of a detection device (as shown in FIGS. 1A-B which are back and front views of a film configuration), trapezoidal or parallelogram (as shown in FIGS. 1C-D which are back and front views of a film configuration), parallel across a side of a device (as shown in FIGS. 1E-F which are back and front views of a film configuration), angled forming an open diamond or facing brackets < > (as shown in FIGS. 1G-H which are back and front views of a film configuration), curved forming an open oval or facing parenthesis ( ) (as shown in FIGS. 1I-J which are back and front views of a film configuration).

Where the detection device is positioned on a screen of the mobile device, the configuration of the two or more electrodes in the transparent film is such that it does not impede the ability to view the screen of the electronic device when the film is applied to the surface of the electronic device and the profile of the electrode is selected to minimize impact on the screen visibility. More particularly, the thickness of the film is such that it does not impede the ability to use, for example, touch screen functionality that might be associated with the electronic device. Where the detection device is configured for positioning on the rear surface of the outer cover of the electronic device, transparency of film is no longer a critical part of the functionality of the detection device. Additionally, a wider variety of electrode designs can be employed including round, oval, square, rectangular, etc. Thus, as will be appreciated by those skilled in the art, the film can be transparent, translucent or opaque depending upon where the film will be positioned, e.g., where the film will be positioned on the display of the electronic device during use or storage a transparent film would be desirable, where the film will be positioned on the exterior casing, transparency would no longer be required.

The two or more electrodes of the configuration of FIG. 1 remain in contact with the electronic device (either the display as shown or the electronic device housing) which enables the electronic device to sense the physiological parameter from the user while the electronic device and the detection device are in communication with each other and in communication with a mammal. The two or more electrodes are in electrical communication with existing electronics on the electronic device, for example capacitive accelerometers, a capacitive touch screen, a resistive touch screen, and surface acoustic wave touch screens.

FIGS. 2A-F illustrate a variety of configurations suitable for a detection device. The detection device 200 is formed from a film 202 having a first side 204 and a second side 206, such as a protective transparent. The detection device 200 includes two or more electrodes 210, 210', one or more microchips adapted and configured to provide computer memory 220 wherein the microchip is configurable to control the operation of the detection device and to store data collected during operation of the detection device, and a microchip 230 configured to provide logic circuitry for wireless communication and enabling communication from the detection device 200 to another electronic device. Chip 230 is adapted and configured to be in electrical communication with the computer memory 220 via a connector 232. Additionally, the computer memory 220 is adapted and configured to be in electrical communication with each of the two or more electrodes 210, 210' via a corresponding connector 222, 222'. A power source 240, such as a lithium battery, can also be provided which is in communication with the computer memory 220 and the chip 230. The power source 240 can also be configured such that it is re-chargeable (e.g., capable of re-charging via application of sunlight or solar power). Additional chips can be provided to provide additional functionality, such as location information. The detection device can be configured such that it is reusable and the power source is rechargeable. The dimensions of the detection device typically range from 8 cm×5 cm×0.2 cm to 15 cm×10 cm×1.5 cm. Although other dimensions can be employed without departing from the scope of the disclosure.

Suitable communication chips 230 include WiFi chips and 3G chips. Any suitable chip can be employed including, but not limited to, WiMAX, Point-to-Multipoint and Point-to-Point Backhaul technologies for a complete indoor and outdoor wireless broadband ecosystems; the CELLULAR SPECIALTIES INC. systems integrator, which provides turnkey indoor coverage systems for Wireless Service Providers (WSP), Enterprise Customers, Public Safety and First Responders; Sonus Networks network transformation IP communications technology which supports multi-device demands; Ruckus Wireless, Inc. which makes Smart Wi-Fi products and Smart Wireless LAN (WLAN) systems; XIRRUS Xirrus, Wi-Fi Array® architecture that displaces both overlay Wi-Fi offerings and switched Ethernet to the desktop; Atheros Communications, Inc. wireless communications products; Barcoding Inc. automatic identification and data collection systems (AIDC) and RFID technology; D-Link Corporation/D-Link Systems, Inc networking, broadband, digital, voice and data communications solutions; Eye-Fi chips; Proxim Wireless Wi-Fi®, WiMAX, Point-to-Multipoint and Point-to-Point Backhaul technologies.

Additionally, EDX Wireless LLC software tools can be used to engineer a suitable chip for the wireless communications network of this application, including wireless broadband, LTE, WiMAX, Wi-Fi, public safety, and other mobile wireless systems.

Suitable computer memory chips 220 include chips manufactured by, for example, Samsung, Seagate, Sandisk, Toshiba.

The two or more electrodes, computer memory, power sources, and/or communication chips can be added to the film during the manufacturing process of the detection device. Electrodes can be made of any suitable conductive material including, but not limited to aluminum, copper, silver and gold. The protective film can be made of any suitable material capable of sticking or adhering, removeably sticking or adhering, or repeatably sticking or adhering to a surface of human, skin and/or a target electronic device, such as a cell phone 808 or smart phone or other portable smart device (where it can be kept for storage when not in use). The protective film can be made from, for example, polyester films, polyolefin films, polyvinyl chloride films, polycarbonate films, cellulosic films, acrylic films, methacrylic films, styrenic films, ceramic films, glass films and suitable co-polymers thereof. One surface of the film typically includes a resin disposed on the surface. Moreover, the film can be a biaxially oriented polyethylene terephthalate film that includes a cured, roughened coating on the second surface 206. The scratch resistant coating can also function as a writing surface. None of these substances are known to produce any significant skin reaction or other health hazards. The protective film can be configured similar to a screen protector such that it is easily applied and removed. GPS chips can also be incorporated, such as GPS chips manufactured by, for example, Ashtech, Eagle GPS, Garmin, and Trimble. The use of GPS chips would facilitate locating a patient who had an abnormal physiological parameter sensed (such as an irregular cardiac rhythm) and transmitted but who, as a result of the parameter, may not be physically able to call for emergency services. As will be appreciated by those skilled in the art, the film can be transparent, translucent or opaque as discussed above and the electrodes can take on a variety of configurations depending on whether the detection device is stored on a screen of an electronic device or on a housing.

During the process of manufacturing a suitable film, two or more electrodes, storage disk and communication chip, can be added to the film (either on a surface or embedded) in such a way that at least a portion of the electrodes are exposed on the surface of the film or the film can also have a coating of adhesive layer containing the active material of opposite distributed there through in finely comminuted form. The polymeric matrix of this coating, apart from adhering firmly to the metal and must be sufficient conductive to form of low resistance internal current path between the two electrodes plate surfaces. The two electrodes are then accessible by a user by touching them, e.g. by adhering the detection device to a skin surface proximate to the heart, placing the detection device on the mammalian body.

In other configurations, the electrodes can be attached to the film in a post-processing or during the film making process step. As will be appreciated by those skilled in the art, the bi-polar electrodes can vary in size (length, width, thickness) depending on the application and the desired signal to be obtained from the patient.

Figures 2A, 2B:
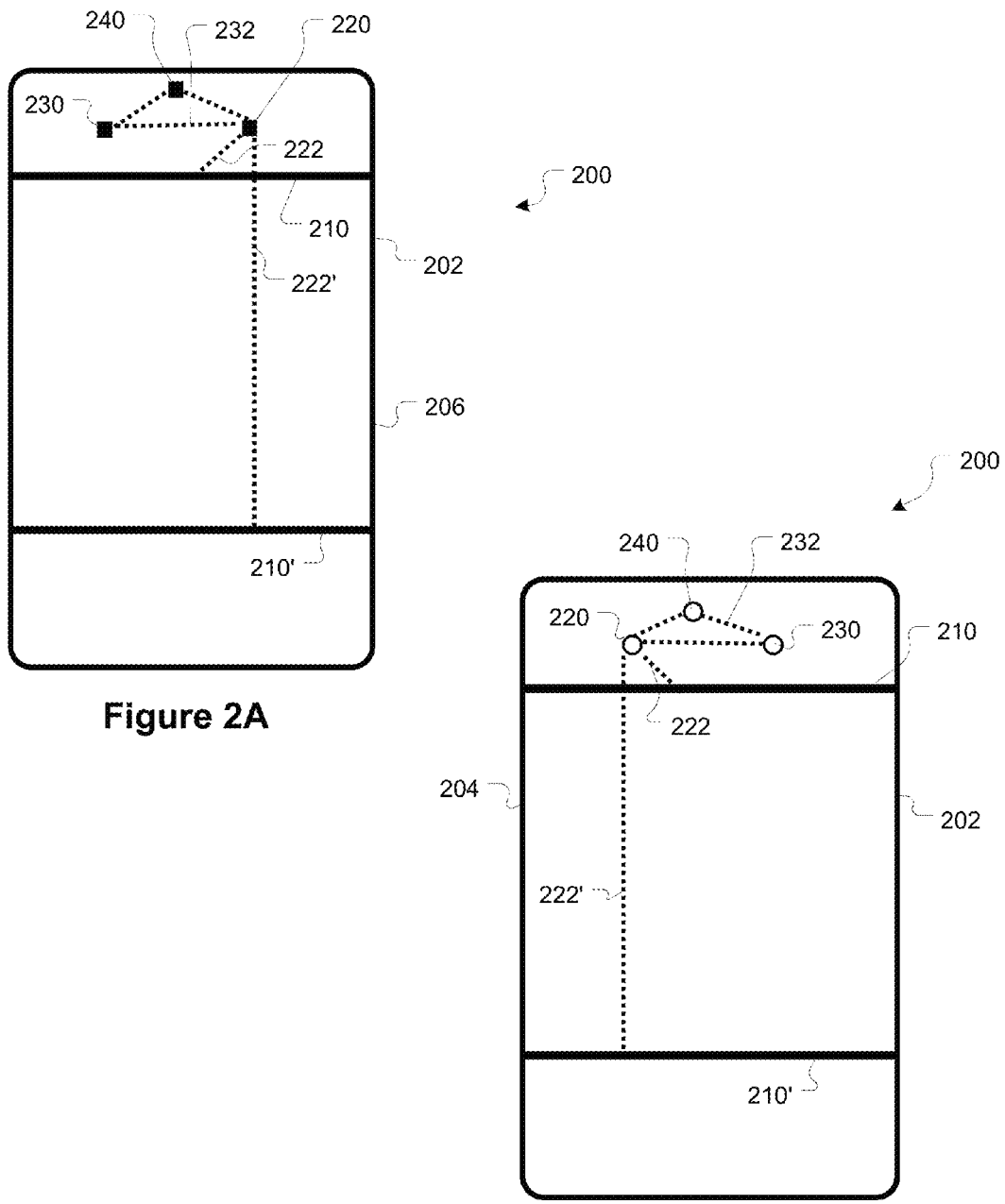
Figure 2E:
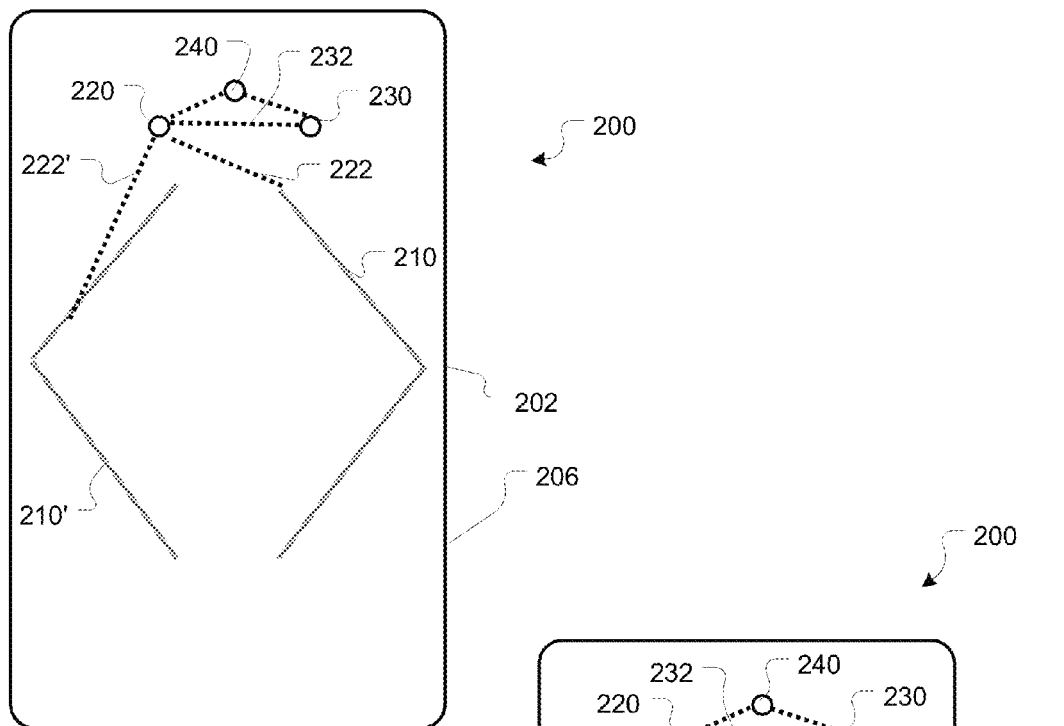
Figure 2F:
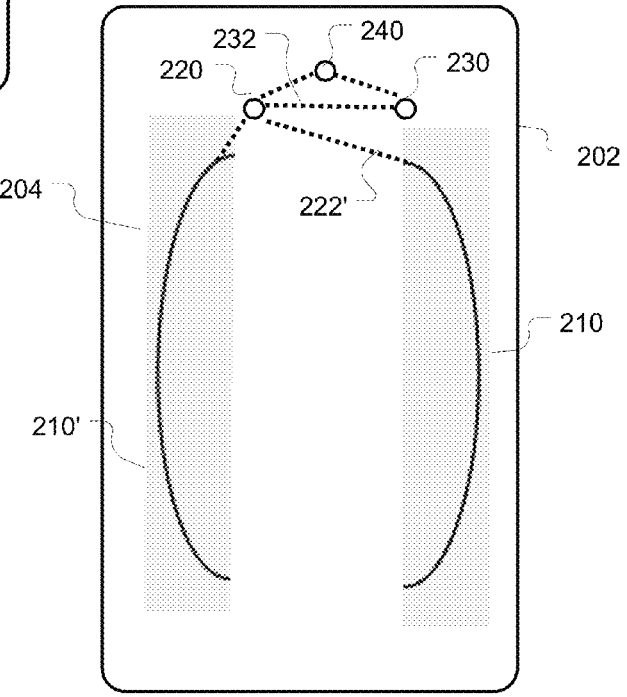

As discussed above, the shape of the film can vary such that it is square, rectangular, round, oval, elliptical, diamond, etc. so that it can easily fit any commercially available cell phone device, having a typical two-dimensional size of from 40 cm$^2$ to 150 cm$^2$. However, other sizes can be employed without departing from the scope of the disclosure as discussed above. In at least some embodiments, the two-dimensional shape of the detection device will substantially conform to the two-dimensional shape of a surface of the electronic device, such as mobile device, to which the detection device is attached. As further illustrated in FIGS. 2A-F the positioning of the two or more electrodes within the film can also take on a wide variety of configurations including, but not limited to, parallel across a top and bottom of a detection device (as shown in FIGS. 2A-B which are back and front views of a film configuration), trapezoidal or parallelogram (as shown in FIG. 2C which is a front view of a film configuration), parallel across a side of a device (as shown in FIG. 2D which is a front view of a film configuration), angled forming an open diamond or facing brackets < > (as shown in FIG. 2E which is a front view of a film configuration), curved forming an open oval or facing parenthesis ( ) (as shown in FIG. 2F which is a front view of a film configuration).

As will be appreciated by those skilled in the art, the electronics of the electronic device can be used to facilitate physiological parameter monitoring—either by being in physical communication with the detection device during the detection process or by sensing a physiological parameter detected by the detection device.

Figure 3A:
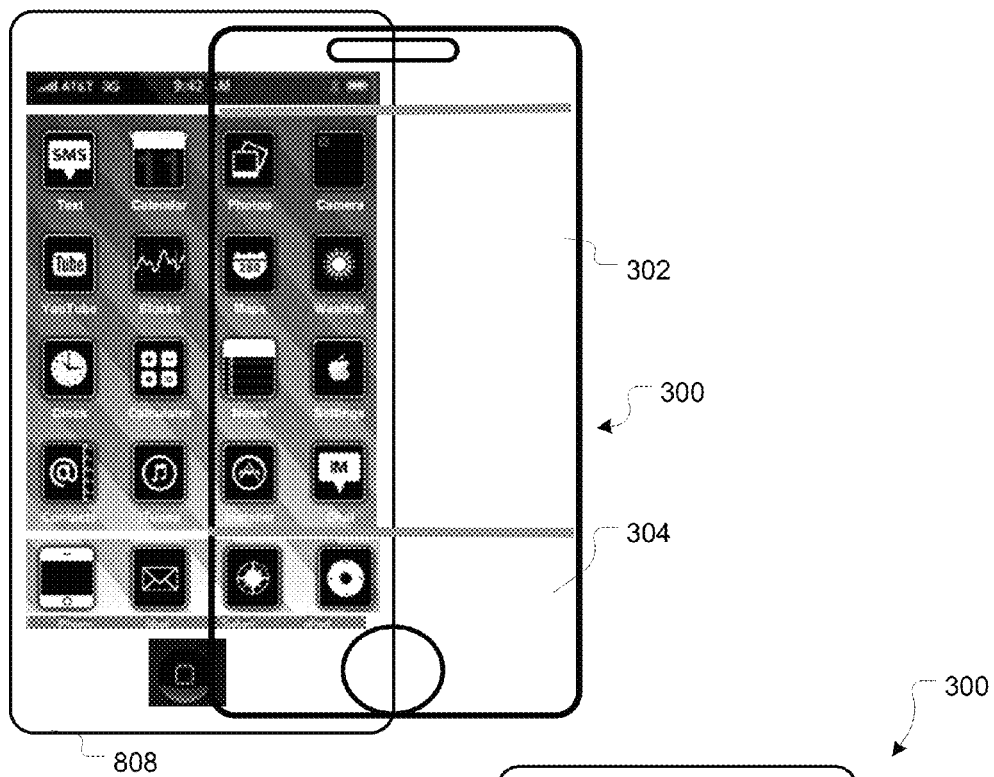
FIGS. 3A-C illustrate a detection device in the process of being applied to a surface of an electronic device such as a smart phone, such as an iPhone®.
Figure 3B:
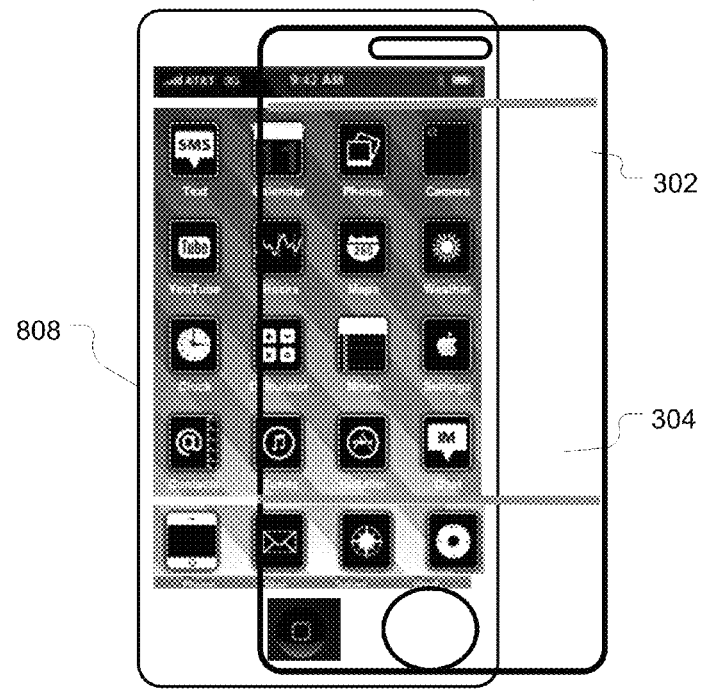
Figure 3C:
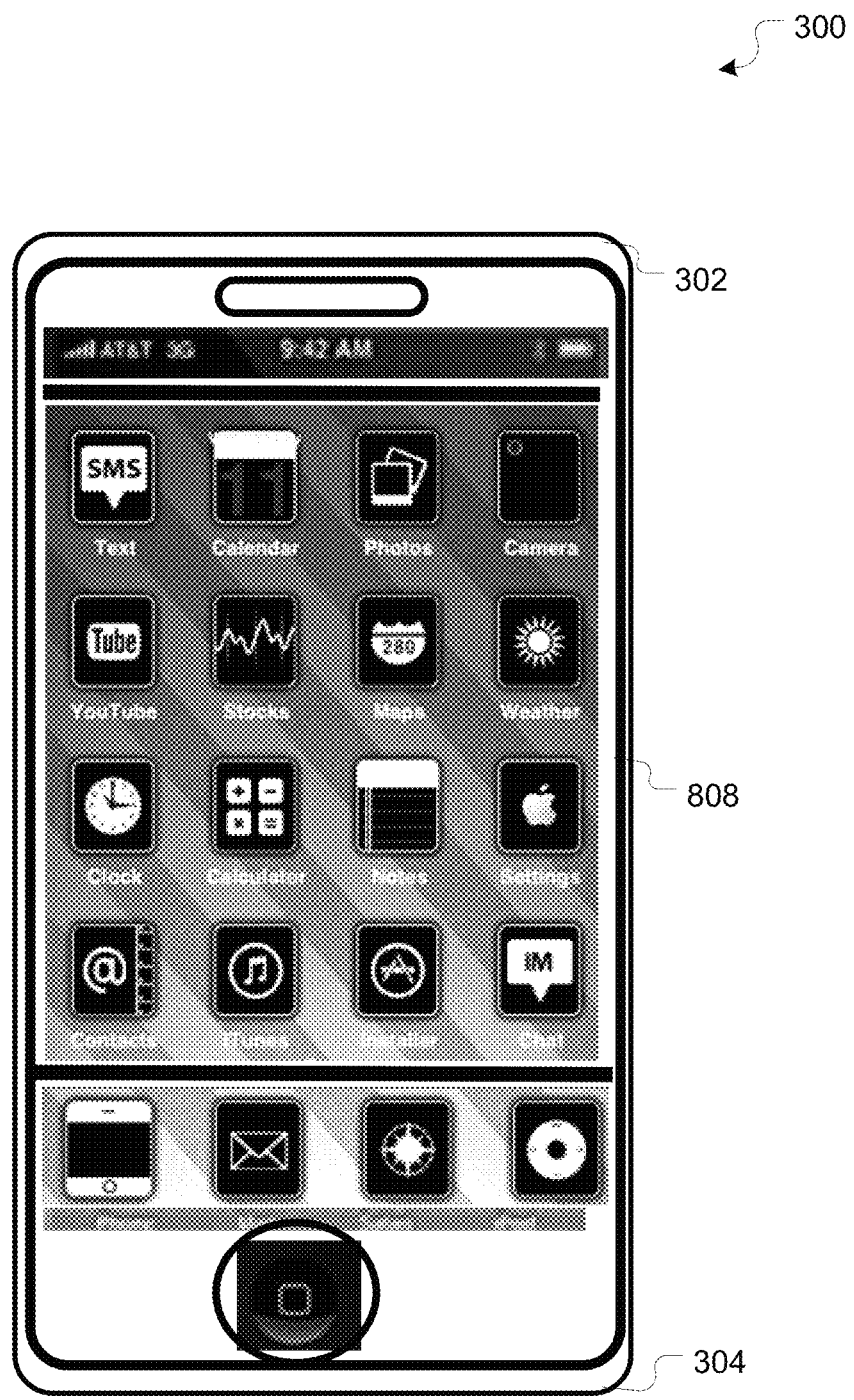

FIGS. 3A-C illustrate a rhythm detector 300 in the process of being applied to a surface of an electronic device such as a smart phone 808', e.g. an iPhone® (Apple, Inc., Cupertino, Calif.). The detection device 300 is formed from a film 302 having a first side 304. The rhythm detector 300 is configured such that it is adherable to a single surface of the electronic device 808'.

Figure 4A:
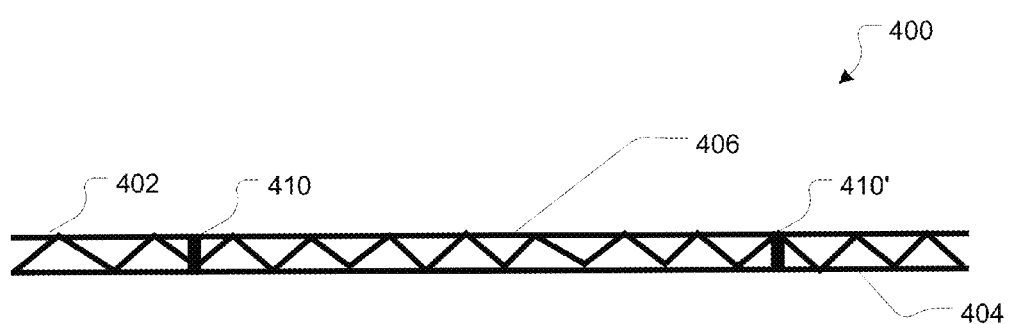
FIG. 4A illustrates a cross-sectional side view of a detection device comprising a film with two electrodes.

FIG. 4A illustrates a side view of a rhythm check detector 400 film 402, having a first side 404, and a second side 406, and as illustrated in FIG. 1 with the at least two electrodes 410, 410' positioned therein. The flat configuration of the rhythm detector 400 film 402 facilitates adhering the rhythm detector to a single surface of the electronic device, as show in FIGS. 3A-C.

Figure 4B:
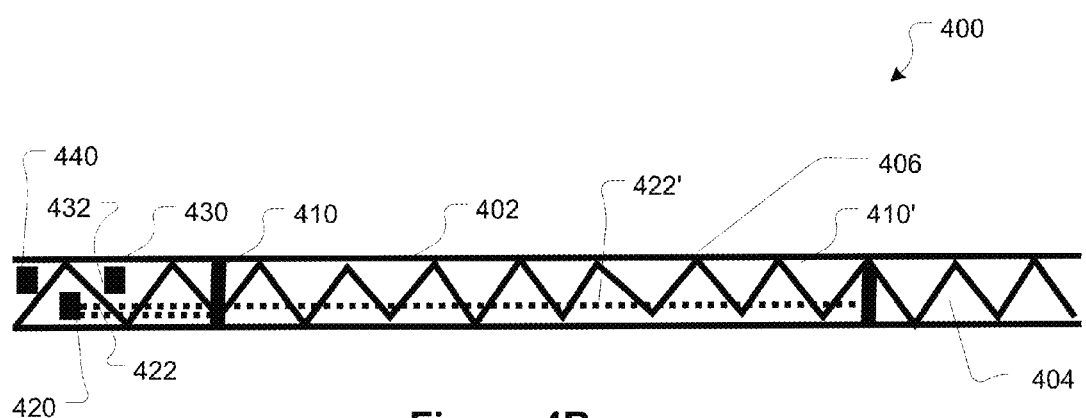
FIG. 4B illustrates a cross-sectional side view of a detection device with two electrodes, a storage disk and at least one wireless communication chip.

FIG. 4B illustrates a side view of a rhythm check detector 400 film 402, having a first side 404, and a second side 406, and as illustrated in FIG. 2 with the at least two electrodes 410, 410', a microchip adapted and configured to provide computer memory 420, and a microchip adapted and configured to provide logic circuitry for wireless communication (such as 3G or WiFi chips) positioned therein. As is known in the art, bipolar electrodes have an anode and a cathode. The anode and the cathode are joined together in a plane via an intermediate, which separates the anode and cathode from direct contact. Conventional fusion welding processes, namely resistance and spot welding, TIG or NIG welding, welding using laser beams and the like, can be used to connect the components of the electrode. A removable layer (not shown) can also be provided to protect the surface of the detection device that contacts the phone during transit. Additionally, the connectors 422, 422' enables the detector to be in electrical communication with the electrodes. A power source 440, such as a lithium battery, can also be provided which is in communication with the computer memory and the chip 430. A connector 432 is provided to electrically connect the chip 430 and the computer memory 420.

II. Methods

Figure 5A:
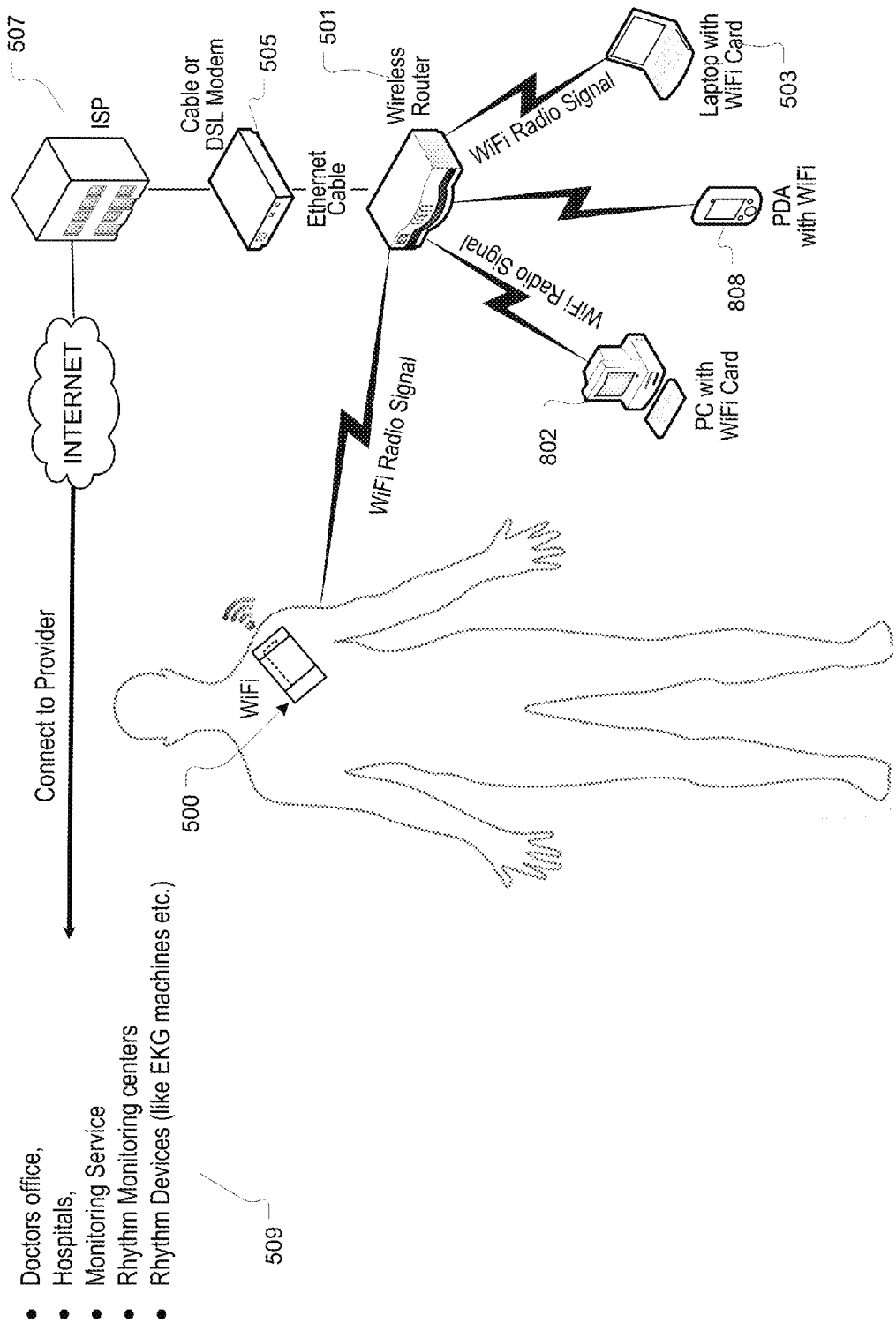
FIGS. 5A-B illustrate representations of a detection device in use.
Figure 5B:
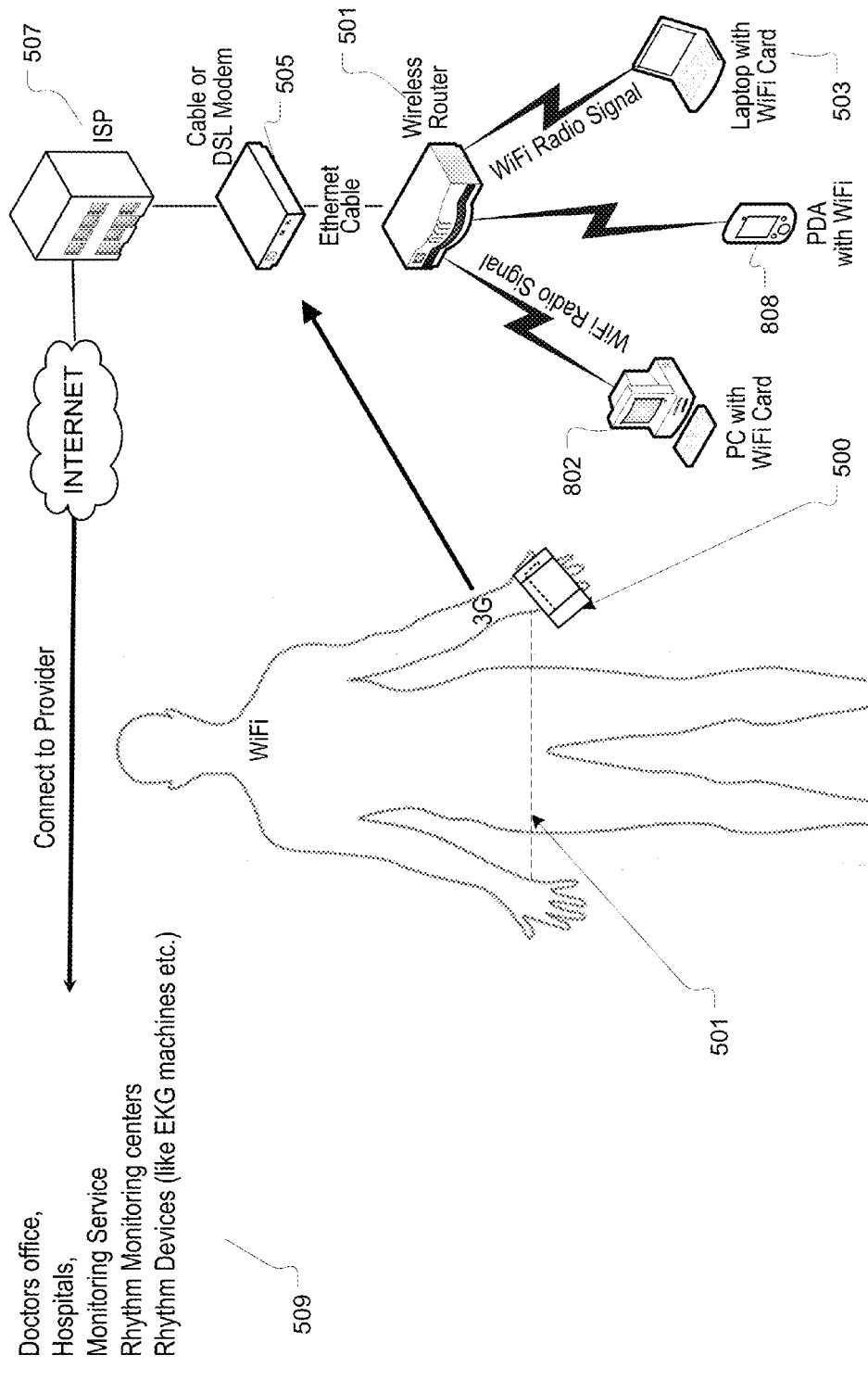

FIGS. 5A-B illustrate representations of a physiological parameter detection device of in use. As illustrated in FIG. 5A, a user places the detection device or an electronic device having a detection device associated therewith in contact with a skin surface (shown here as the chest below the clavicle bone) to sense one or more physiological parameters (e.g., impedance, heart rhythm and/or pulse). Other physiological characteristics can also be detected including, for example, temperature, respiration, blood pressure, vasomotor activity, physical activity, and body position. The one or more sensed physiological parameters can then be stored on the detection device or the electronic device and/or transmitted to another device. Software can be provided either on the detection device or the associated electronic device that detects the parameter, analyzes the parameter, and/or transmits the parameter. More specifically, for the configuration of FIG. 1, when in use, the combination of the film and electronic device are, for example, placed on a mammalian surface wherein the physiological parameter is detection by the electronic device through the use of the film. For the configuration of FIG. 2, when in use, the film is removed from the electronic device surface and then, for example, placed on a mammalian surface wherein the physiological parameter is detection by the film and communicated to another device (such as the electronic device).

Where the one or more physiological parameters is transmitted, a wireless signal from the detection device or electronic device is sent to a wireless router 501 which can be in communication (wired or wirelessly) with one or more of a personal computer (such as a personal computer with a wireless card 802), a smart phone or PDA with WiFi capability 808", a laptop 503, and an Ethernet connection (via cable or DSL modem 505) to an ISP 507 which in turn provides a connection to a doctor's office, a hospital, a monitoring service, a rhythm monitoring center, and/or other rhythm devices or impedance detection devices 509.

As illustrated in FIG. 5B, a user can alternatively activate the device 500 by touching the device with both hands (shown by dashed line 501). For the configuration of FIG. 1, when in use, the film is positioned on a surface of the electronic device and then the combination of the electronic device and film is, for example, held by a user wherein the physiological parameter is detection by the electronic device through the use of the electronics of the film. For the configuration of FIG. 2, when in use, the film is removed from the electronic device and then, for example, held by a user wherein the physiological parameter is detection by the film and communicated to another device (such as an electronic device).

Figure 6:
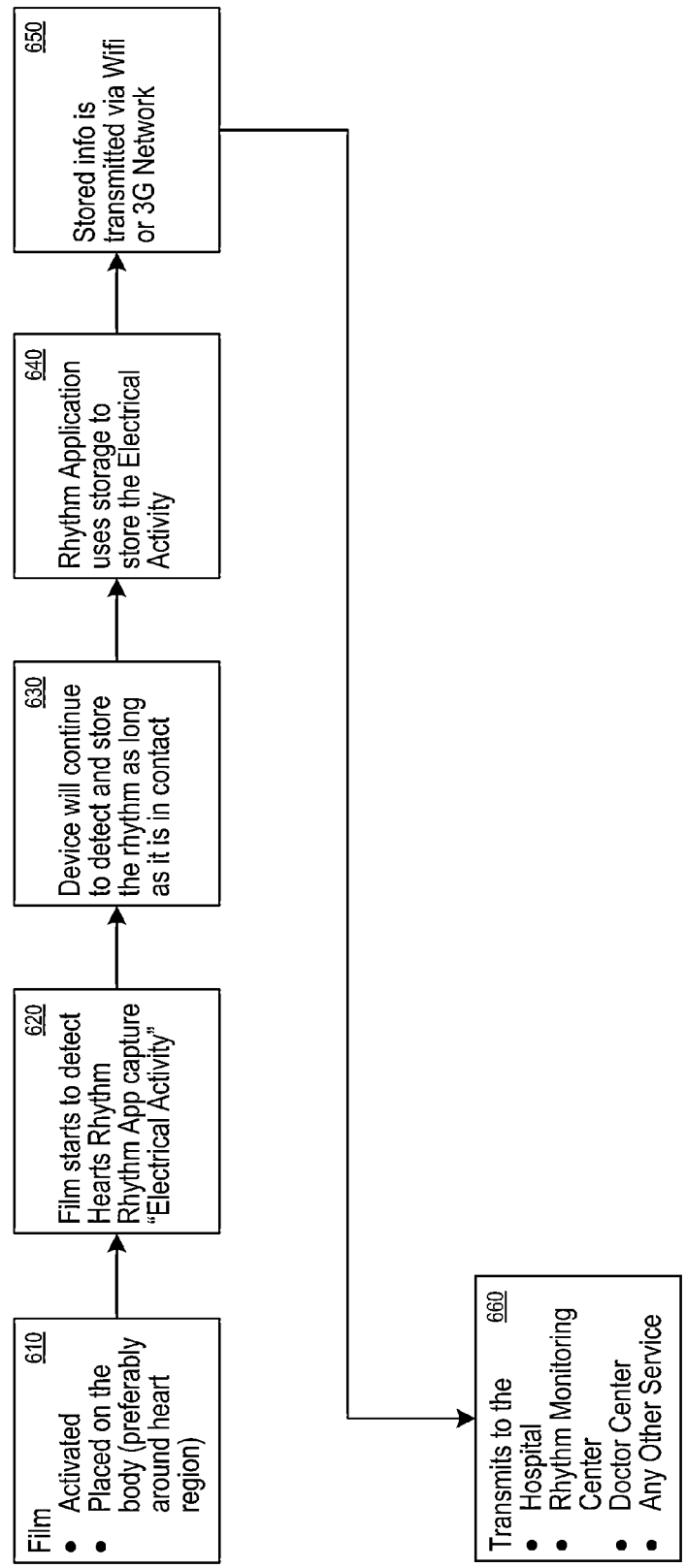
FIG. 6 illustrates a flow chart of a method of using the detection device disclosed.

FIG. 6 illustrates a flow chart of a method of using a detection device. When software is activated and the detection device is placed, for example, on the heart 610, the detection device will use the film's two or more electrodes to capture an electrical conduction signal generated by electrical stimulus in the heart 620. The detection device continues to detect and store the heart rhythm as long as the film is in contact with the patient 630. An application associated with the electronic device (such as a smart phone), uses storage to store the electrical activity captured by the film 640. The two or more electrodes on the film then detect and transmit the signal to the hand-held electronic device which then stores the data or transmit the data to another location. So, for example, stored information can then be transmitted via WiFi or 3G Network to another location 650. Other locations include a hospital, a rhythm monitoring center, a doctor's office, or any other location or service that is desirable 660.

Another method of using a detection device and software that implements the method provides that when the software is activated and the detection device is placed, for example, on or near the heart, the detection device will use the film's two or more electrodes to capture an electrical conduction signal generated by electrical stimulus in the heart. The two or more electrodes on the film then detect and transmit the physiological parameter data to the hand-held electronic device which then stores the data or transmit the data to another location. The detection device can also store data about, for example, the electrical activity of a heart, on a storage disk incorporated into the detector. The information can then be transmitted to another location (e.g., hospital, rhythm monitoring center, doctor's office, or any other location). Transmission of the captured physiological parameter data can be in lieu of storage, concurrent with storage, or at a subsequent point in time (e.g., delayed). In some instances, the third party (e.g., hospital, doctor) can be configured to communicate with the device to retrieve information (stored or in the process of being captured) on demand. Thus the information can be transferred (pushed) to the third party or retrieved (pulled) by the third party.

Figure 7:
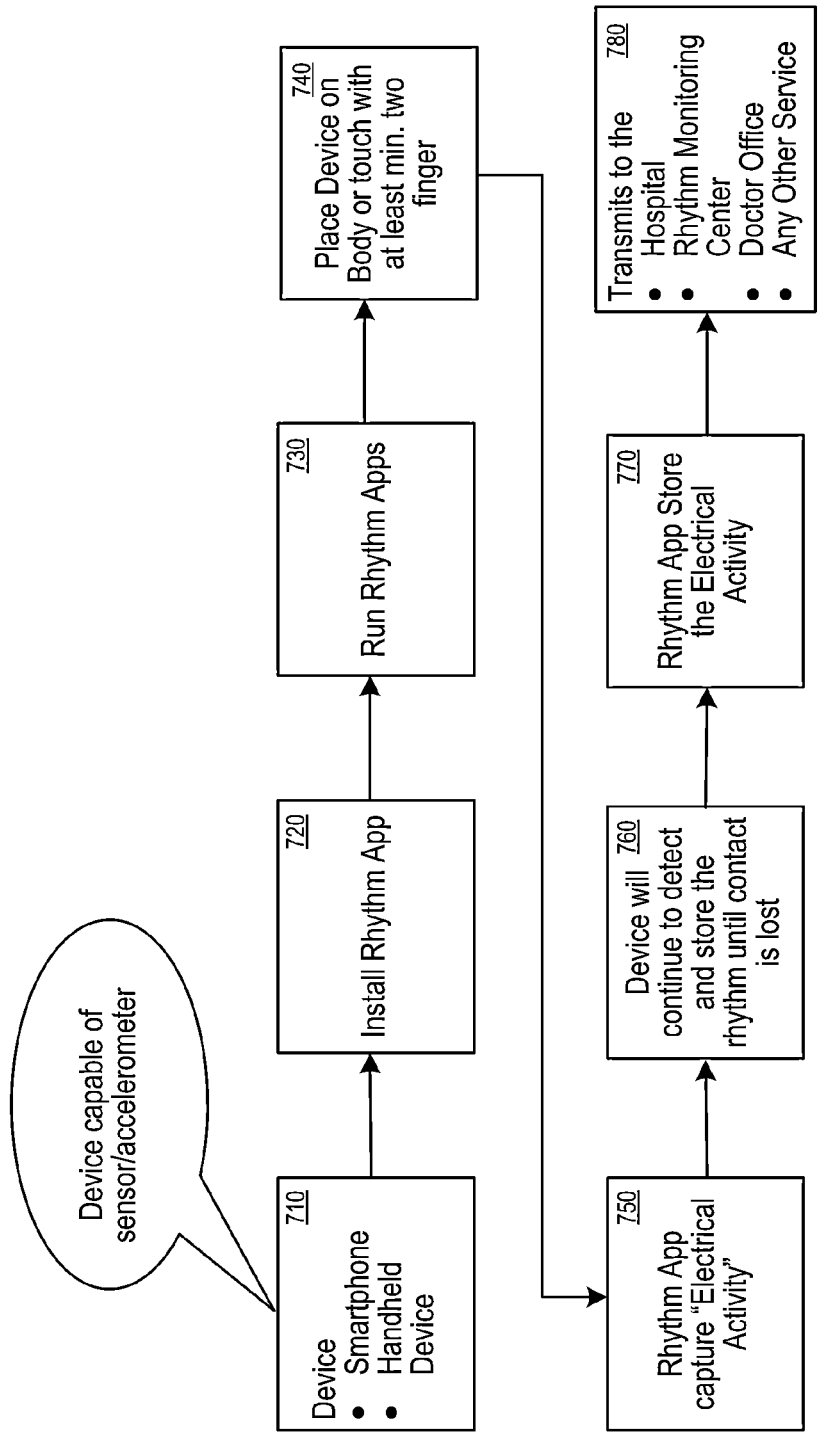
FIG. 7 is a block diagram illustrating a method of operation for a detection device.

FIG. 7 illustrates a flow chart which tracks installation of a software application on a mobile electronic device to transmitting data to a third location. An electronic device, such as a smart phone or handheld device, which can include, for example, a sensor, accelerometer, capacitive accelerometers, a capacitive touch screen, a resistive touch screen, and/or surface acoustic wave touch screens is selected 710. A software application is installed on the electronic device 720 which is configured to obtain information from a detection device. The user then initiates operation of the application 730, or operation can be initiated automatically when a signal received from a detection device. The detection device, or combination of the detection device and electronic device, can then be placed on a mammalian body or touched with at least two fingers 740. The application then captures data about the electrical activity 750. The detection device is configurable such that it will continued to detect and store the rhythm until contact is lost 760. The rhythm information can then be stored 770. After storage, or concurrently with storage, the information can be transmitted to another location 780.

III. Computing and Network Environments to Achieve a Desired Technical Effect or Transformation As will be appreciated by those skilled in the art, modular and scalable system employing one or more of the cardiac rhythm detection devices discussed above can be provided which are comprised of a controller and more than one cardiac rhythm detection devices. Controller communicates with each cardiac rhythm detection device over a communication media. Communication media may be a wired or wireless point-to-point or multi-drop configuration. Examples of wired communication media include Ethernet, USB, and RS-232. Alternatively communication media may be wireless including radio frequency (RF) and optical. Networked devices can be particularly useful in some situations. For example, networked devices that provide monitoring results to a care provider (such as a doctor) can facilitate background analysis of compliance of a patient with a recommended treatment protocols which could then trigger earlier intervention by a healthcare provider when results begin trending in a clinically undesirable direction. Additionally, automatic messages in response to sample measurements can be generated to either the patient and/or to the care provider. In some instances, automatic messages may be generated by the system to either encourage behavior (e.g., a text message or email indicating a patient is on track) or discourage behavior. Other automated messages could be either email or text messages providing pointers and tips for any lifestyle changes. The networked communication system therefore enables background health monitoring and early intervention which can be achieved at a low cost with the least burden to health care practitioners.

Figure 8A:
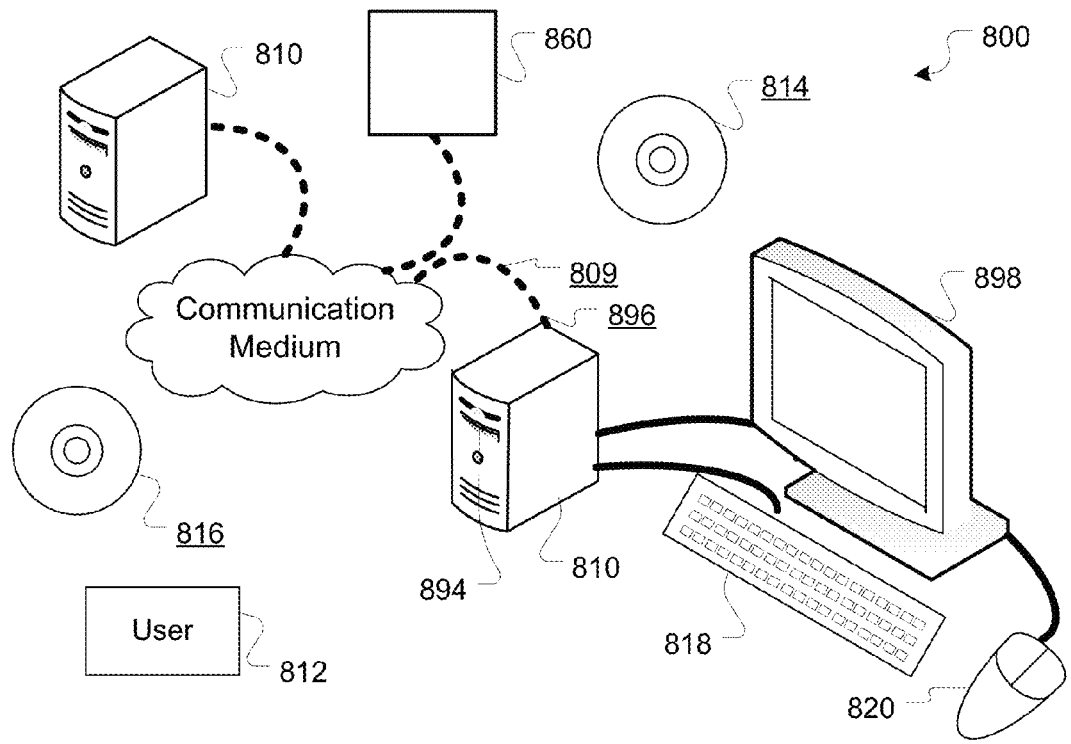
FIG. 8A is a block diagram showing a representative example of a logic device through which a dynamic modular and scalable system can be achieved.

To further appreciate the networked configurations of multiple cardiac rhythm detection device in a communication network, FIG. 8A is a block diagram showing a representative example logic device through which a browser can be accessed to control and/or communication with cardiac rhythm detection device described above. A computer system (or digital device) 800, which may be understood as a logic apparatus adapted and configured to read instructions from media 814 and/or network port 896, is connectable to a server 810, and has a fixed media 816. The computer system 800 can also be connected to the Internet or an intranet. The system includes central processing unit (CPU) 880, disk drives 894, optional input devices, illustrated as keyboard 818 and/or mouse 820 and optional monitor 898'. Data communication can be achieved through, for example, communication medium 809 to a server 810 at a local or a remote location. The communication medium 809 can include any suitable means or mechanism of transmitting and/or receiving data. For example, the communication medium can be a network connection, a wireless connection, or an internet connection. It is envisioned that data relating to the use, operation or function of the one or more cardiac rhythm detection device (shown together for purposes of illustration here as 860) can be transmitted over such networks or connections. The computer system can be adapted to communicate with a user (users include healthcare providers, physicians, lab technicians, nurses, nurse practitioners, patients, and any other person or entity which would have access to information generated by the system) and/or a device used by a user. The computer system is adaptable to communicate with other computers over the Internet, or with computers via a server. Moreover the system is configurable to activate one or more devices associated with the network (e.g., diagnostic devices and/or cardiac rhythm detection device) and to communicate status and/or results of tests performed by the devices and/or systems.

As is well understood by those skilled in the art, the Internet is a worldwide network of computer networks. Today, the Internet is a public and self-sustaining network that is available to many millions of users. The Internet uses a set of communication protocols called TCP/IP (i.e., Transmission Control Protocol/Internet Protocol) to connect hosts. The Internet has a communications infrastructure known as the Internet backbone. Access to the Internet backbone is largely controlled by Internet Service Providers (ISPs) that resell access to corporations and individuals.

The Internet Protocol (IP) enables data to be sent from one device (e.g., a phone, smart Phone, a Personal Digital Assistant (PDA), a computer, etc.) to another device on a network. There are a variety of versions of IP today, including, e.g., IPv4, IPv6, etc. Other IPs are no doubt available and will continue to become available in the future, any of which can, in a communication network adapted and configured to employ or communicate with one or more cardiac rhythm detection devices, be used without departing from the scope of the disclosure. Each host device on the network has at least one IP address that is its own unique identifier and acts as a connectionless protocol. The connection between end points during a communication is not continuous. When a user sends or receives data or messages, the data or messages are divided into components known as packets. Every packet is treated as an independent unit of data and routed to its final destination—but not necessarily via the same path.

The Open System Interconnection (OSI) model was established to standardize transmission between points over the Internet or other networks. The OSI model separates the communications processes between two points in a network into seven stacked layers, with each layer adding its own set of functions. Each device handles a message so that there is a downward flow through each layer at a sending end point and an upward flow through the layers at a receiving end point. The programming and/or hardware that provides the seven layers of function is typically a combination of device operating systems, application software, TCP/IP and/or other transport and network protocols, and other software and hardware.

Typically, the top four layers are used when a message passes from or to a user and the bottom three layers are used when a message passes through a device (e.g., an IP host device). An IP host is any device on the network that is capable of transmitting and receiving IP packets, such as a server, a router or a workstation. Messages destined for some other host are not passed up to the upper layers but are forwarded to the other host. The layers of the OSI model are listed below. Layer 7 (i.e., the application layer) is a layer at which, e.g., communication partners are identified, quality of service is identified, user authentication and privacy are considered, constraints on data syntax are identified, etc. Layer 6 (i.e., the presentation layer) is a layer that, e.g., converts incoming and outgoing data from one presentation format to another, etc. Layer 5 (i.e., the session layer) is a layer that, e.g., sets up, coordinates, and terminates conversations, exchanges and dialogs between the applications, etc. Layer-4 (i.e., the transport layer) is a layer that, e.g., manages end-to-end control and error-checking, etc. Layer-3 (i.e., the network layer) is a layer that, e.g., handles routing and forwarding, etc. Layer-2 (i.e., the data-link layer) is a layer that, e.g., provides synchronization for the physical level, does bit-stuffing and furnishes transmission protocol knowledge and management, etc. The Institute of Electrical and Electronics Engineers (IEEE) sub-divides the data-link layer into two further sub-layers, the MAC (Media Access Control) layer that controls the data transfer to and from the physical layer and the LLC (Logical Link Control) layer that interfaces with the network layer and interprets commands and performs error recovery. Layer 1 (i.e., the physical layer) is a layer that, e.g., conveys the bit stream through the network at the physical level. The IEEE sub-divides the physical layer into the PLCP (Physical Layer Convergence Procedure) sub-layer and the PMD (Physical Medium Dependent) sub-layer.

Wireless networks can incorporate a variety of types of mobile devices, such as, e.g., cellular and wireless telephones, PCs (personal computers), laptop computers, wearable computers, cordless phones, pagers, headsets, printers, PDAs, etc. and suitable for use in a system or communication network that includes one or more cardiac rhythm detection devices. For example, mobile devices may include digital systems to secure fast wireless transmissions of voice and/or data. Typical mobile devices include some or all of the following components: a transceiver (for example a transmitter and a receiver, including a single chip transceiver with an integrated transmitter, receiver and, if desired, other functions); an antenna; a processor; display; one or more audio transducers (for example, a speaker or a microphone as in devices for audio communications); electromagnetic data storage (such as ROM, RAM, digital data storage, etc., such as in devices where data processing is provided); memory; flash memory; and/or a full chip set or integrated circuit; interfaces (such as universal serial bus (USB), coder-decoder (CODEC), universal asynchronous receiver-transmitter (UART), phase-change memory (PCM), etc.), global positioning (GPS) data, etc. Other components can be provided without departing from the scope of the disclosure.

Wireless LANs (WLANs) in which a mobile user can connect to a local area network (LAN) through a wireless connection may be employed for wireless communications between one or more cardiac rhythm detection devices. Wireless communications can include communications that propagate via electromagnetic waves, such as light, infrared, radio, and microwave. There are a variety of WLAN standards that currently exist, such as Bluetooth®, IEEE 802.11, and the obsolete HomeRF.

By way of example, Bluetooth products may be used to provide links between mobile computers, mobile phones, portable handheld devices, personal digital assistants (PDAs), and other mobile devices and connectivity to the Internet. Bluetooth is a computing and telecommunications industry specification that details how mobile devices can easily interconnect with each other and with non-mobile devices using a short-range wireless connection. Bluetooth creates a digital wireless protocol to address end-user problems arising from the proliferation of various mobile devices that need to keep data synchronized and consistent from one device to another, thereby allowing equipment from different vendors to work seamlessly together.

An IEEE standard, IEEE 802.11, specifies technologies for wireless LANs and devices. Using 802.11, wireless networking may be accomplished with each single base station supporting several devices. In some examples, devices may come pre-equipped with wireless hardware or a user may install a separate piece of hardware, such as a card, that may include an antenna. By way of example, devices used in 802.11 typically include three notable elements, whether or not the device is an access point (AP), a mobile station (STA), a bridge, a personal computing memory card International Association (PCMCIA) card (or PC card) or another device: a radio transceiver; an antenna; and a MAC (Media Access Control) layer that controls packet flow between points in a network.

In addition, Multiple Interface Devices (MIDs) may be utilized in some wireless networks. MIDs may contain two independent network interfaces, such as a Bluetooth interface and an 802.11 interface, thus allowing the MID to participate on two separate networks as well as to interface with Bluetooth devices. The MID may have an IP address and a common IP (network) name associated with the IP address.

Wireless network devices may include, but are not limited to Bluetooth devices, WiMAX (Worldwide Interoperability for Microwave Access), Multiple Interface Devices (MIDs), 802.11x devices (IEEE 802.11 devices including, 802.11a, 802.11b and 802.11g devices), HomeRF (Home Radio Frequency) devices, Wi-Fi (Wireless Fidelity) devices, GPRS (General Packet Radio Service) devices, 3 G cellular devices, 2.5 G cellular devices, GSM (Global System for Mobile Communications) devices, EDGE (Enhanced Data for GSM Evolution) devices, TDMA type (Time Division Multiple Access) devices, or CDMA type (Code Division Multiple Access) devices, including CDMA2000. Each network device may contain addresses of varying types including but not limited to an IP address, a Bluetooth Device Address, a Bluetooth Common Name, a Bluetooth IP address, a Bluetooth IP Common Name, an 802.11 IP Address, an 802.11 IP common Name, or an IEEE MAC address.

Wireless networks can also involve methods and protocols found in, Mobile IP (Internet Protocol) systems, in PCS systems, and in other mobile network systems. With respect to Mobile IP, this involves a standard communications protocol created by the Internet Engineering Task Force (IETF). With Mobile IP, mobile device users can move across networks while maintaining their IP Address assigned once. See Request for Comments (RFC) 3344. NB: RFCs are formal documents of the Internet Engineering Task Force (IETF). Mobile IP enhances Internet Protocol (IP) and adds a mechanism to forward Internet traffic to mobile devices when connecting outside their home network. Mobile IP assigns each mobile node a home address on its home network and a care-of-address (CoA) that identifies the current location of the device within a network and its subnets. When a device is moved to a different network, it receives a new care-of address. A mobility agent on the home network can associate each home address with its care-of address. The mobile node can send the home agent a binding update each time it changes its care-of address using Internet Control Message Protocol (ICMP).

In basic IP routing (e.g., outside mobile IP), routing mechanisms rely on the assumptions that each network node always has a constant attachment point to the Internet and that each node's IP address identifies the network link it is attached to. Nodes include a connection point, which can include a redistribution point or an end point for data transmissions, and which can recognize, process and/or forward communications to other nodes. For example, Internet routers can look at an IP address prefix or the like identifying a device's network. Then, at a network level, routers can look at a set of bits identifying a particular subnet. Then, at a subnet level, routers can look at a set of bits identifying a particular device. With typical mobile IP communications, if a user disconnects a mobile device from the Internet and tries to reconnect it at a new subnet, then the device has to be reconfigured with a new IP address, a proper netmask and a default router. Otherwise, routing protocols would not be able to deliver the packets properly.

Figure 8B:
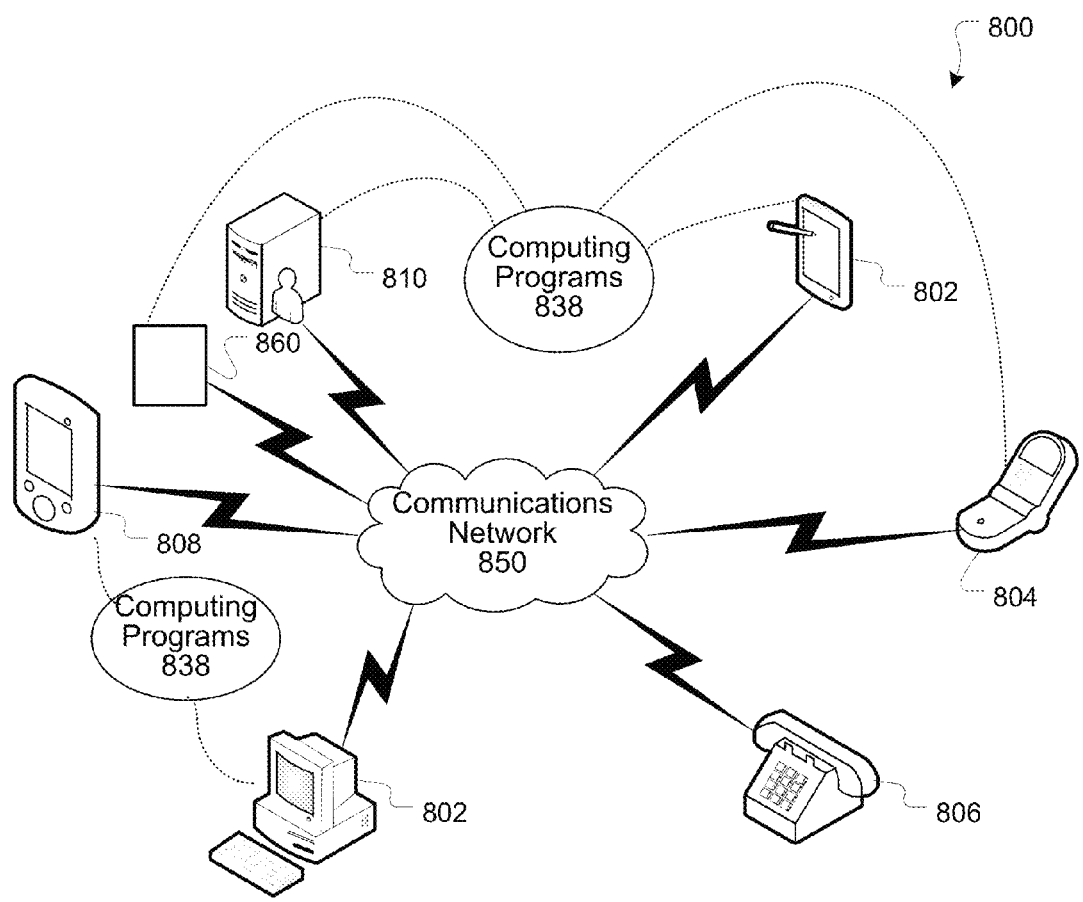
FIG. 8B is a block diagram showing the cooperation of exemplary components of a system suitable for use in a system where dynamic data analysis and modeling is achieved.

Computing system 800, described above, can be deployed as part of a computer network that includes one or more devices 860, such as cardiac rhythm detection devices disclosed herein. In general, the description for computing environments applies to both server computers and client computers deployed in a network environment. FIG. 8b illustrates an exemplary illustrative networked computing environment 800, with a server in communication with client computers via a communications network 850. As shown in FIG. 8b, server 810 may be interconnected via a communications network 850 (which may be either of, or a combination of a fixed-wire or wireless LAN, WAN, intranet, extranet, peer-to-peer network, virtual private network, the Internet, or other communications network) with a number of client computing environments such as tablet personal computer 822, mobile telephone 804, telephone 806, personal computer 802', and personal digital assistant 808'''. In a network environment in which the communications network 850 is the Internet, for example, server 810 can be dedicated computing environment servers operable to process and communicate data to and from client computing environments via any of a number of known protocols, such as, hypertext transfer protocol (HTTP), file transfer protocol (FTP), simple object access protocol (SOAP), or wireless application protocol (WAP). Other wireless protocols can be used without departing from the scope of the disclosure, including, for example Wireless Markup Language (WML), DoCoMo i-mode (used, for example, in Japan) and XHTML Basic. Additionally, networked computing environment 800 can utilize various data security protocols such as secured socket layer (SSL) or pretty good privacy (PGP). Each client computing environment can be equipped with operating system 838 operable to support one or more computing applications, such as a web browser (not shown), or other graphical user interface (not shown), or a mobile desktop environment (not shown) to gain access to server computing environment 800.

In operation, a user (not shown) may interact with a computing application running on a client computing environment to obtain desired data and/or computing applications. The data and/or computing applications may be stored on server computing environment 800 and communicated to cooperating users through client computing environments over exemplary communications network 850. A participating user may request access to specific data and applications housed in whole or in part on server computing environment 800. These data may be communicated between client computing environments and server computing environments for processing and storage. Server computing environment 800 may host computing applications, processes and applets for the generation, authentication, encryption, and communication data and applications and may cooperate with other server computing environments (not shown), third party service providers (not shown), network attached storage (NAS) and storage area networks (SAN) to realize application/data transactions.

IV. Kits

Bundling all devices, tools, components, materials, and accessories needed to use a cardiac rhythm device may enhance the usability and convenience of the devices. Kit could also include a protective film, a film with two bipolar electrodes, a software application on a memory device or instructions for downloading software from, for example, an application store, such as the Apple® App Store or Android Application Store. Software once installed on the smart phone device would get activated and be ready for use with the cardiac rhythm detection device. Suitable kits for detecting the cardiac rhythm can also include, for example, prepackaged alcohol swabs, one or more lint free cloths, and a cling adhesion material.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A detection device adapted to capture a physiological parameter comprising:
   a transparent film with an insulating upper surface and a lower surface characterized in that the transparent film is removeably adherable to a single surface of an electronic device; and
   two or more conductive elements wherein at least two conductive elements of the two or more conductive elements are bipolar electrodes, in electrical communication with the removeably adherable lower surface and electrically isolated by the insulating upper surface, wherein the detection device is in wireless communication with the electronic device when the detection device is adhered to the single surface of the electronic device.

2. The detection device of claim 1 further wherein the two or more conductive elements include a first elongated conductive element and a second elongated conductive element, electrically separated from the first elongated conductive element.

3. The detection device of claim 1 further wherein the transparent film has a first dimension of from about 40 cm to 150 cm and a second dimension of from about 40 cm to 150 cm and is square or rectangular.

4. The detection device of claim 1 wherein the two or more conductive elements are a first elongated conductive element and a second elongated conductive element positioned at opposing ends of the film.

5. The detection device of claim 1 wherein the two or more conductive elements are a first elongated conductive element and a second elongated conductive element positioned parallel each other in a plane.

6. The detection device of claim 1 wherein the two or more conductive elements are a first elongated conductive element and a second conductive element having a shape selected from the group consisting of straight, bracket, and curved.

7. The detection device of claim 1 further comprising one or more of computer memory, microchip, connector, power source, or communication chip.

8. A kit for physiological characteristic detection comprising:
- a detection device having a transparent film with an insulating upper surface and a lower surface characterized in that the transparent film is removeably adherable to a single surface of an electronic device, two or more conductive elements wherein at least two conductive elements of the two or more conductive elements are bipolar electrodes, in electrical communication with the removeably adherable lower surface and electrically isolated by the insulating upper surface, wherein the detection device is in wireless communication with the electronic device when the detection device is adhered to the single surface of the electronic device;
- a software application; and one or more of the following alcohol swabs; or
- a lint cloth.

9. A networked apparatus comprising:
- an electronic device comprising: a memory;
- a processor;
- a communicator; and
- a display; and
- a detection device having a transparent film with an insulating upper surface and a lower surface characterized in that the transparent film is removeably adherable to a single surface of the electronic device, two or more conductive elements wherein at least two conductive elements of the two or more conductive elements are bipolar electrodes, in electrical communication with the removeably adherable lower surface and electrically isolated by the insulating upper surface, wherein the detection device is in wireless communication with the electronic device when the detection device is adhered to the single surface of the electronic device.

10. A communication system, comprising:
- a detection device having a transparent film with an insulating upper surface and a lower surface characterized in that the transparent film is removeably adherable to a single surface of an electronic device, two or more conductive elements wherein at least two conductive elements of the two or more conductive elements are bipolar electrodes, in electrical communication with the removeably adherable lower surface and electrically isolated by the insulating upper surface, wherein the detection device is in wireless communication with the electronic device when the detection device is adhered to the single surface of the electronic device;
- a server computer system;
- a measurement module on the server computer system for permitting a transmission of a measurement from the detection device over a network; and
- at least one of
  - an API engine connected to at least one of a system for detecting physiological parameters or the detection device to create a message about the measurement and transmit the message over an API integrated network to a recipient having a predetermined recipient user name,
  - an SMS engine connected to at least one of the system for detecting physiological parameters or the detection device to create an SMS message about the measurement and transmit the SMS message over the network to a recipient device having a predetermined measurement recipient telephone number, or
  - an email engine connected to at least one of the system for detecting physiological parameters or the detection device to create an email message about the measurement and transmit the email message over the network to a recipient email having a predetermined recipient email address.

11. The communication system of claim 10, further comprising a storing module on the server computer system for storing the measurement in a detection device server database.

12. The communication system of claim 11, wherein the detection device is connectable to the server computer system over at least one of a mobile phone network or an Internet network, and a browser on a measurement recipient electronic device is used to retrieve an interface on the server computer system.

13. The communication system of claim 11, further comprising: an interface on the server computer system, the interface being retrievable by an application on a mobile device.

14. The communication system of claim 11, wherein the server computer system is connectable over a cellular phone network to receive a response from a measurement recipient mobile device.

15. The communication system of claim 11, further comprising:
- a downloadable application residing on a measurement recipient mobile device, the downloadable application transmitting a response and a measurement recipient phone number ID over a cellular phone network to the server computer system, the server computer system utilizing the measurement recipient phone number ID to associate the response with an SMS measurement.

16. The communication system of claim 11, further comprising:
- a transmissions module that transmits the measurement over a network other than a cellular phone SMS network to a measurement recipient user computer system, in parallel with the measurement that is sent over the cellular phone SMS network.

17. A communication system comprising:
- an electronic device comprising a memory, a processor, a communicator and a display;
- a detection device having a transparent film with an insulating upper surface and a lower surface characterized in that the transparent film is removeably adherable to a single surface of the electronic device, two or more conductive elements wherein at least two conductive elements of the two or more conductive elements are bipolar electrodes, in electrical communication with the removeably adherable lower surface and electrically isolated by the insulating upper surface, wherein the detection device is in wireless communication with the electronic device when the detection device is adhered to the single surface of the electronic device;
- a server computer system in communication with the electronic device;
- a measurement module on the server computer system for permitting a transmission of a measurement from the detection device over a network; and
- at least one of
  - an API engine connected to at least one of the electronic device or the detection device to create a message about the measurement and transmit the message over an API integrated network to a recipient having a predetermined recipient user name,
  - an SMS engine connected to at least one of the electronic device or the detection device to create an SMS message about the measurement and transmit the SMS message over the network to a recipient device having a predetermined measurement recipient telephone number, or an email engine connected to at least one of the electronic device or the detection device to create an email message about the measurement and transmit the email message over the network to a recipient email having a predetermined recipient email address.

18. The communication system of claim 17, further comprising a storing module on the server computer system for storing the measurement on a detection device server database.

19. The communication system of claim 17, wherein the detection device is connectable to the server computer system over at least one of a mobile phone network or an Internet network, and a browser on the electronic device is used to retrieve an interface on the server computer system.

20. The communication system of claim 17, wherein the electronic device is connected to the server computer system over a cellular phone network.

21. The communication system of claim 17, wherein the electronic device is a mobile device.

* * * * *